United States Patent
Kolar et al.

(10) Patent No.: US 6,610,299 B1
(45) Date of Patent: *Aug. 26, 2003

(54) GLYCOSYL-ETOPOSIDE PRODRUGS, A PROCESS FOR PREPARATION THEREOF AND THE USE THEREOF IN COMBINATION WITH FUNCTIONALIZED TUMOR-SPECIFIC ENZYME CONJUGATES

(75) Inventors: Cenek Kolar, Marburg (DE); Jörg Czech, Marburg (DE); Klaus Bosslet, Marburg (DE); Gerhard Seemann, Marburg (DE); Hans-Harald Sedlacek, Marburg (DE); Dieter Hoffmann, Marburg (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/325,955

(22) Filed: Oct. 19, 1994

Related U.S. Application Data

(63) Continuation-in-part of application No. 08/219,901, filed on Mar. 30, 1994, now abandoned, which is a continuation-in-part of application No. 08/117,343, filed on Sep. 7, 1993, now abandoned, which is a division of application No. 08/117,343, which is a continuation-in-part of application No. 08/061,502, filed on May 14, 1993, now abandoned, which is a continuation of application No. 07/982,421, filed on Nov. 27, 1992, now abandoned, which is a continuation of application No. 07/841,829, filed on Feb. 26, 1992, now abandoned, which is a continuation of application No. 07/599,517, filed on Oct. 18, 1990, now abandoned.

(30) Foreign Application Priority Data

Oct. 19, 1989 (DE) .......................................... 39 35 016
Feb. 28, 1991 (DE) .......................................... 41 06 389

(51) Int. Cl.$^7$ ............................................ A61K 39/44
(52) U.S. Cl. ................ 424/179.1; 424/178.1; 514/2; 514/4; 514/23; 536/1.11
(58) Field of Search .................. 424/179.1, 178.1; 514/23, 2, 4; 536/1.11

(56) References Cited

U.S. PATENT DOCUMENTS

| | | | |
|---|---|---|---|
| 3,524,844 A | 8/1970 | Keller-Juslen et al. | 536/18.1 |
| 4,547,567 A | 10/1985 | Umezawa et al. | 536/18.1 |
| 4,727,136 A | 2/1988 | Jennings et al. | 530/395 |
| 4,757,138 A | 7/1988 | Fujii et al. | 536/18.1 |
| 4,935,504 A | 6/1990 | Saulnier et al. | 536/18.1 |
| 4,975,278 A | 12/1990 | Senter et al. | 536/18.1 |
| 5,036,055 A | 7/1991 | Ohnuma et al. | 514/27 |
| 5,041,424 A | 8/1991 | Saulnier et al. | 536/18.1 |
| 5,045,451 A | 9/1991 | Uhr et al. | 435/7.23 |
| 5,057,313 A | * 10/1991 | Shih et al. | |
| 5,106,951 A | 4/1992 | Morgan, Jr. et al. | 530/391.9 |
| 5,122,368 A | 6/1992 | Greenfield et al. | 530/327 |
| 5,164,311 A | * 11/1992 | Gupta | |
| 5,561,119 A | * 10/1996 | Jacquesy et al. | 514/34 |

FOREIGN PATENT DOCUMENTS

| | | | |
|---|---|---|---|
| CA | A 2025899 | 7/1990 | |
| DE | 0 3826562 A1 | 2/1988 | |
| DE | A3909799.4 | 7/1990 | |
| EP | 0 141 079 | 5/1985 | |
| EP | A 0172 045 | 2/1986 | |
| EP | 0 302 473 A2 | 2/1989 | |
| FR | A 2 591 895 | 6/1987 | |
| JP | 63-192793 | 8/1988 | 536/18.1 |
| WO | 88/07378 | * 10/1988 | |
| WO | WO 88/07378 | 10/1988 | |
| WO | WO A 9108770 | 6/1991 | |
| WO | 92/19639 | * 11/1992 | |

OTHER PUBLICATIONS

Rudinger, Peptide Hormones (Ed. JA Parsons) Jun. 1976 pp. 1–6.*

Kashimata et al, Experientia, 43, pp. 191–192.*

Schroder et al, The Peptides, Vol. 1, pp. xxii–xxiii, (1965).*

Fleminger et al., "Oriented Immobilization Of Periodate–Oxidized Monoclonal Antibodies On Amino And Hydrazide Derivatives Of Eupergit C," Applied Biochem. Biotechnol., Vol. 23, pp. 132–137 (1990).

Chatterjee et al., "Idiotypic Antibody Immunotherapy Of Cancer," Cancer Immunol. Immnother., Chapter 38: 75–82 (1994).

W. J. Harris et al., "Therapeutic Antibodies—The Coming Of Age," Tibtech, Vol. 11, pp. 42–44 (1993).

L. Reichmann et al., "Reshaping Human Antibodies For Therapy," Nature, Vol. 332, pp. 323–327 (Mar. 24, 1988).

S. Morrison, "Transfectomas Provide Novel Chimeric Antibodies," Science, Vol. 229, pp. 1202–1207 (1985).

Washington Post, "Prostate Cancer Blood Test Supasses Traditional Physical Exam In Study," (Aug. 25, 1993).

Dillman, Anals of Internal Medicine, Vol. 111, No. 7, pp. 592–603 (1989).

Borrebaeck, Journal of Immunological Methods, Vol. 123, pp. 157–165 (1989).

Osband et al., Immunology Today, Vol. 11, No. 6, pp. 193–195 (1990).

Waldmann, Science, Vol. 252, pp. 1657–1662 (1991).

Martin et al., Cancer Research, Vol. 46, pp. 2189–2192 (1986).

(List continued on next page.)

Primary Examiner—Bennett Celsa
(74) Attorney, Agent, or Firm—Finnegan, Henderson, Farabow, Garrett and Dunner, L.L.P.

(57) ABSTRACT

The present invention relates to glycosyl-etoposide prodrugs, a process for the preparation thereof and the use thereof in combination with functionalized tumor-specific enzyme conjugates for treating cancers.

16 Claims, 13 Drawing Sheets

OTHER PUBLICATIONS

Chaudhary et al., Proc. Natl. Acad. Sci. USA, Vol. 84, pp. 4538–4542 (1987).

Gregoriadis et al., Tibtech, Vol. 11, p. 440–442 (1993).

A.H. Blair et al., "Linkage of Cytotoxic Agents to Immunoglobulins," J. of Immunolog. Methods, Vol. 59, 1983, pp. 129–143.

T.I. Ghose et al., "Preparation of Antibody–Linked Cytotoxic Agents," Methods in Enzymology, Vol. 93, 1983, pp. 280–333.

K.J. Dean et al., "Studies on Human Liver α–Galactosidases: Purification of Galactosidase A and its Enzymatic Properties with Glycolipid and Oligosaccharide Substrates," J. of Biol. Chem., Vol. 254, 1979, pp. 9994–10000.

K. Ho, "Human β–glucuronidase. Studies On The Effects Of pH And Bile Acids in Regard To its Role In The Pathogenesis Of Cholelithiasis," Biochimica et Biophysica Acta, Vol. 827, 1985, pp. 197–206.

G. Dawson et al., Substrate Specificity of Human α–L–Fucosidase, Archives of Biochemistry and Biophysics, Vol. 184, 1977, pp. 12–23.

C. Noeske et al., "β–D–Mannosidase from Human Placenta: Properties and Partial Purification," Hoppe–Seyler's Z. Physiol. Chem., Vol. 364, Dec. 1983, pp. 1645–1651.

N.–G. Asp et al., "Acid α–Glucosidase from Human Gastrointestinal Mucosa–Separation and Characterization," Scand. J. Clin. Lab. Invest., Vol. 33, pp. 239–245.

A. Orlacchio et al., "β–N–Acetyl–D–glucosaminidase Isoenzymes From Human Amnionic Membranes," Clinica Chimica Acta, Vol. 159, 1986, pp. 279–289.

F. Furbish et al., "Enzyme replacement therapy in Gauncher's disease: Large–scale purification of glucocerebrosidase suitable for human administration," Proc. Natl. Acad. Sci. USA, Vol. 74, No. 8, Aug. 1977, pp. 3560–3563.

W. Rohrborn et al., "Human Placenta α–N–Acetylglucosaminidase: Purification, Characterization and Demonstration of Multiple Recognition Forms," Hopp–Seyler's Z. Physiol. Chem. Vol. 359, Oct. 1978, pp. 1353–1362.

R. Salvayre et al., "α–Galactosidases et α–N–Acetylgalactosaminidase Bases Biochimigues de la Maladie de Fabry," Pathol. Biol., Vol. 32, 1984, pp. 269–284. (Abstract only).

G. A. Grabowski et al., "Comparative Physical, Kinetic and Immunologic Properties of the Acidic and Neutral α–D–Mannosidase Isozymes from Human Liver," Enzyme, Vol. 25, 1980, pp. 13–25.

K. Hande et al., "Metabolism and Excretion of Etoposide in Isolated, Perfused Rat Liver Models," Cancer Research, Vol. 48, No. 20, pp. 5692–5695, Oct. 15, 1988.

K. Hande et al., "Identification of Etoposide Glucuronide as a Major Metabolite of Etoposide in the Rat and Rabbit," Cancer Research, Vol. 48, No. 7, pp. 1829–1834, Apr. 1, 1988.

J.J.M. Holthuis et al., "Determination of the Glucuronide(s) of the Antineoplastic Agents Etoposide," Methodological Surveys In Biochemistry Anal., Vol. 16 (Bioactive Analytes, inc. CNS Drugs, Peptides and Enantiomers), pp. 389–393.

Hermentin et al., "Investigations with Monoclonal Antibody Drug (Anthracycline) Conjugates," Behring Inst. Mitt., No. 82, 197–215 (1986).

Righetti et al., "Biochemical And Clinical Applications Of Isoelectric Focusing," Elsevier Scientific Publ. Co. (1979).

Horsfall et al., "Purification Of Human Autoantibodies From Cross–Linked Antigen Immunosorbents," J. Immun. Meth., Vol. 104, pp. 43–49 (1987).

Towbin et al., "Electrophoretic Transfer Of Proteins From Polyacrylamide Gels To Nitrocellulose Sheets: Procedure And Some Applications," Proc. Natl. Acad. Sci. USA Vol. 76, pp. 4350–4354 (1979).

Oshima et al., "Cloning, Sequencing, And Expression Of cDNA For Human β–Glucuronidase," Proc. Natl. Acad. Sci. USA, Vol. 84, pp. 685–689 (1987).

Bosslet et al., "Quantitative Considerations Supporting The Irrelevance Of Circulating Serum CEA For The Immunoscintigraphic Visualization Of CEA Expressing Carcinomas," Eur. J. Nucl. Med., Vol. 14, pp. 523–528 (1988).

Walter et al., "Anti–Idiotypic Antibodies: Powerful Tools In Diagnosis And Therapy," Behring Inst. Mitt., Vol. 82, pp. 182–192 (1988).

Seemann, G., et al., "Antibody Enzyme Fusion Protein For Antibody Directed Enzyme Prodrug Therapy—Carcinoembryonic Antigen–Specific Monoclonal Antibody And β–Glucuronidase Fusion Protein," Biotechnology Abstracts, Abstract No. 92–14076 (1991).

Daniels et al., "Purification and Characterization of a Cytosolic Broad Specificity β–Glucosidase from Human Liver," J. of Biol. Chem., Vol. 256, 1981, pp. 13004–13013.

Clark, William R., "The Experimental Foundation of Modern Immunology", pp. 458–462.

Gerken, M., et al., "Glycosyl Prodrugs of Anthracyclines, A Process For The Preparation Thereof And The Use Thereof In Combination With Functionalized Tumor–Specific Enzyme Conjugates," Abstract, Australian Patent Application No. AU–A–70117/91 (1991).

Cunningham et al., "Antibody Engineering—How To Be Human," Tibtech, Vol. 10 (1992).

Cordell et al., "Immunoenzymatic Labelling Of Monoclonal Antibodies Using Immune Complexes Of Alkaline Phosphatase And Monoclonal Anti–Alkaline Phosphatase (APAAP Complexes)," The Journal of Histochemistry and Cytochemistry, Vol. 32, pp. 219–229 (1984).

Stahl et al., "Evidence For Specific Recognition Sites Mediating Clearance Of Lysosomal Enzymes in vivo," Proc. Natl. Acad. Sci. USA, Vol. 76, No. 11, pp. 4045–4049 (1976).

* cited by examiner

GLYCOSYL-ETOPOSIDE PRODRUGS, A PROCESS FOR PREPARATION THEREOF AND THE USE THEREOF IN COMBINATION WITH FUNCTIONALIZED TUMOR-SPECIFIC ENZYME CONJUGATES

This application is a continuation-in-part of application Ser. No. 08/117,343, filed Sep. 7, 1993 (abn), which is a continuation of application Ser. No. 07/982,421, filed Nov. 27, 1992, now abandoned, which was a continuation of application Ser. No. 07/599,517, filed Oct. 18, 1990, now abandoned. This application is also a continuation-in-part of application Ser. No. 08/219,901, filed Mar. 30, 1994 now abandoned, which is a division of application Ser. No. 08/117,343 now abandoned. This application is also a continuation-in-part of application Ser. No. 08/061,502, filed May 14, 1993 now abandoned, which is a continuation of application Ser. No. 07/841,829, filed Feb. 26, 1992, now abandoned. The above applications are incorporated herein by reference in their entirety.

FIELD OF THE INVENTION

The present invention relates to glycosyl-etoposide prodrugs, a process for the preparation thereof and the use thereof in combination with functionalized tumor-specific enzyme conjugates for treating cancers, and specifically relates to 4'-O-glycosyl-etoposides as prodrugs which can be cleaved by the action of tumor-specific enzyme conjugates to give cytotoxic active substances, the liberated active substance being suitable, by reason of its cytostatic activity, for treating cancers.

The present invention further relates to enzyme conjugates for prodrug activation, including fusion proteins of the general formula huTuMAb-L-β-Gluc, where huTuMAb is a humanized or human tumor-specific monoclonal antibody, a fragment or a derivative thereof, L is linker, and β-Gluc comprises human β-glucuronidase. These fusion proteins are prepared by genetic manipulation. huTuMAb ensures the specific localization of tumors, L connects the huTuMAb to β-Gluc in such a way that the specific properties of the two fusion partners are not impaired, and β-Gluc activates a suitable prodrug compound by elimination of glucuronic acid, where a virtually autologous system for use in humans is provided by the humanized or human fusion partners.

BACKGROUND OF THE INVENTION

The combination of prodrug and tumor-specific antibody-enzyme conjugates for use as therapeutic agents is described in the specialist literature. This has entailed injection of antibodies which are directed against a particular tissue and to which a prodrug-cleaving enzyme is covalently bonded into an animal which contains the transplanted tissue, and subsequently administering a prodrug compound which can be activated by the enzyme. The prodrug is converted by the action of the antibody-enzyme conjugate, which is anchored to the tissue, into the cytotoxin which exerts a cytotoxic effect on the transplanted tissue.

A therapeutic system which contains two components, an antibody-enzyme component and a prodrug component that can be activated by the enzyme is described in WO 88/07378. In this case, the use of non-mammalian enzymes is described for the preparation of the antibody-enzyme conjugates, and that of endogenous enzymes is ruled out because of non-specific liberation of active compound. Since the exogenous enzymes are recognized by the body as foreign antigens, the use thereof is associated with the disadvantage of an immune response to these non-endogenous substances, which can result in the enzyme immobilized on the antibody being inactivated, or possibly, the entire conjugate being eliminated. In addition, in this case p-bis-N-(2-chloroethyl) amino-benzylglutamic acid and derivatives thereof are used as prodrug, and the chemical half-life thereof is only 5.3 to 16.5 hours. It is a disadvantage for a prodrug to be chemically unstable because of the side effects to be expected.

A therapeutic system which contains two components and in which the antibody-enzyme conjugate located on the tumor tissue cleaves a prodrug compound to form a cytotoxic active compound is likewise described in EPA 0302473 A2. The combined use of etoposide 4'-phosphate and derivatives thereof as prodrug and of antibody-immobilized alkaline phosphatases for liberating the etoposides, which is described therein, inter alia, is disadvantageous because of the presence of large amounts of endogenous alkaline phosphatases in the serum. As described in DE 38265662 A1, the etoposide 4'-phosphates have already been used alone as therapeutic antitumor agents, with the phosphatases present in the serum liberating the etoposide from the prodrug.

DESCRIPTION OF THE INVENTION

It has emerged, surprisingly, that the synthetically prepared, hitherto unobtainable compound 4'-O-alpha-D-glucopyranosyl-etoposide can be cleaved in vitro into etoposide and D-glucose with the enzyme alpha-glucosidase as well as a tumor-specific antibody-glucosidase conjugate.

Based on this finding, and taking into account the disadvantages, described above, of prior art combinations of prodrugs and antibody-enzyme conjugates, the object of the present invention was to prepare synthetic, enzymatically cleavable 4'-O-glycosyl-etoposides as well as functionalized tumor-specific enzymes to cleave them, and to test the pharmacological utility of the combination of the two components in suitable mammalian test models. This object has been achieved by preparing 4'-O-glycosyl-etoposides of formula I and functionalized tumor-specific enzymes of formula II which, on combined use thereof, exhibit cytostatic activity.

The invention thus relates to 4'-O-glycosyl-etoposides of the formula I

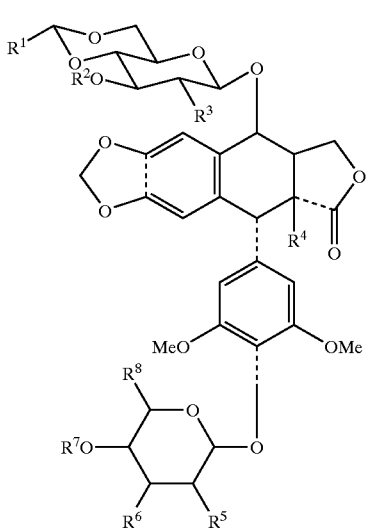

in which
R$^1$ is a methyl, benzyl or 2-thienyl group,
R$^2$ is a hydrogen atom, an acyl or tri-C$_1$–C$_4$-alkylsilyl protective group,
R$^3$ is a hydroxl group, an acyl or tri-C$_1$–C$_4$-alkylsilyl protective group which is bonded via an oxygen atom, an amino, acetylamino, benzyloxycarbonylamino or dimethylamino group, $R^4$ is a hydrogen atom or a methyl group, $R^5$ is a hydrogen atom, a hydroxyl group, an acyl or tri-$C_1$–$C_4$-alkylsilyl protective group which is bonded via an oxygen atom, or an amino, benzyloxycarbonylamino, azido or acetylamino group, $R^6$ is a hydroxyl group, an acyl or tri-$C_1$–$C_4$-alkylsilyl protective group which is bonded via an oxygen atom, or an amino, benzyloxycarbonylamino or azido group, $R^7$ is a hydrogen atom, an acyl or tri-$C_1$–$C_4$-alkylsilyl protective group, and $R^8$ is a methyl or hydroxymethyl group or an acyl protective group which is bonded via a methyleneoxy group, or a benzyloxycarbonyl group, where an acyl protective group means an acetyl, mono-, di- or trihalogenoacetyl group with halogen meaning fluorine or chlorine;

and functionalized tumor-specific enzymes of the formula II $$A\text{—}Sp\text{—}E \qquad \text{II}$$

in which

A is an antibody or one of the fragments thereof, which have specificity for a tumor-associated antigen, or is a biomolecule which accumulates in a tumor, such as EGF (epidermal growth factor), TGF-α (transforming growth factor a), PDGF (platelet derived growth factor), IGF I+II (insulin like growth factor I+II) or a+b FGF (acidic+basic fibroblast growth factor), E is a glycosidase which is not immunogenic or is of low immunogenicity, preferably mammalian glycosidase, as α-or β-glucosidase, α-galactosidase, α- or β-mannosidase, α-fucosidase, N-acetyl-α-galactosaminidase, N-acetyl-β-/N-acetyl-α-glucosaminidase or β-glucuronidase, Sp (spacer) is a polypeptide spacer or a bifunctional sulfide- or disulfide-containing group of the formula III or IV $$X(S)_n Y \qquad \text{III}$$

$$X(S)_n \qquad \text{IV}$$

in which

X is —CO—$R^9$—(N-succinimido)- or —C(=R)—$CH_2$—$CH_2$— with $R^9$ being —$CH_2$—$CH_2$—, 1,4-cyclohexylidene, 1,3- or 1,4-phenylene or methoxycarbonyl- or chloro-1,4-phenylene and R being O or NH, Y is —C(=$R^{10}$)—$CH_2$—$CH_2$—, where $R^{10}$ has the stated meaning, and n is 1 or 2.

Preferred within the scope of the invention are compounds of the formula I in which the radicals $R^1$ is a methyl, benzyl or 2-thienyl group, $R^2$ is a hydrogen atom, an acetyl or chloroacetyl group or a tri-$C_1$–$C_4$-alkylsilyl protective group, $R^3$ is a hydroxyl group, an acetyl, chloroacetyl or tri-$C_1$–$C_4$-alkylsilyl protective group which is bonded via an oxygen atom, or an amino, acetylamino, benzyloxycarbonylamino or dimethylamino group, $R^4$ is a hydrogen atom or a methyl group, $R^5$ is a hydrogen atom, a hydroxyl group, or an acetyl, chloroacetyl or tri-$C_1$–$C_4$-alkylsilyl protective group which is bonded via an oxygen atom, or an amino, benzyloxycarbonylamino, azido or acetylamino group, $R^6$ is a hydroxyl group, an acetyl, chloroacetyl or tri-$C_1$–$C_4$-alkylsilyl protective group which is bonded via an oxygen atom, or an amino, benzyloxycarbonylamino or azido group, $R^7$ is a hydrogen atom, an acetyl, chloroacetyl or tri-$C_1$–$C_4$-alkylsilyl protective group, and $R^8$ is a methyl, hydroxymethyl, acetyloxy or chloroacetyloxymethyl group or a benzyloxycarbonyl group.

Also preferred within the scope of the invention are functionalized tumor-specific enzyme conjugates of the formula II in which A is an antibody or fragment thereof, which have specificity for a tumor-associated antigen, or is a biomolecule which accumulates on or in the tumor, such as EGF (epidermal growth factor), TGF-α (transforming growth factor α), PDGF (platelet derived growth factor), IGF I+II (insulin like growth factor I+II), a+b FGF (acidic+basic fibro-blast growth factor), E is a glycosidase which is not immunogenic or has low immunogenicity, preferably a mammalian glycosidase, for example an α- or β-glucosidase, α-galactosidase, α- or β-mannosidase, α-fucosidase, N-acetyl-α-galactosaminidase, N-acetyl-β-/N-acetyl-α-glucosaminidase or β-glucuronidase, and Sp is a polypeptide spacer or a bifunctional disulfide-containing group of the formula III or IV in which X is —CO—$R^9$—(N-succinimido)- or —C(=$R^{10}$)—$CH_2$—$CH_2$— with $R^9$ being —$CH_2$—$CH_2$— or 1,4-phenylene and $R^{10}$ being O or NH, Y is —C(=$R^{10}$)—$CH_2$—$H_2$—, where $R^{10}$ has the stated meaning, and n is 1 or 2.

Of these preferred functionalized tumor-specific enzyme conjugates, it has been found that certain tumor-specific antibody-glucosidase conjugates, or fusion proteins, comprising a humanized or human tumor-specific monoclonal antibody, or a fragment or derivative thereof, linked to human β-glucuronidase, and prepared by genetic manipulation, are particularly advantageous, because they are virtually autologous. Moreover, it has been found that the catalytic activity of β-glucuronidase in such fusion proteins at pH 7.4 (i.e. physiological conditions) is significantly higher than that of the native enzyme when the fusion protein is bound to the antigen via the V region. Furthermore, a fusion protein with only one hinge region (see Table 4 and Example 22) can be generated by genetic manipulation in high yield because most of the product which is formed results as one band (in this case with molecular weight 125,000) and can be easily purified by affinity chromatography with anti-idiotype MAbs or anti-glucuronidase MAbs.

Accordingly, especially preferred tumor-specific enzyme conjugates of the invention are fusion proteins of the formula V $$\text{huTuMAb-L-β-Gluc} \qquad \text{V}$$

in which huTuMAb is a humanized or human tumor-specific monoclonal antibody or a fragment or a derivative thereof, and preferably comprises the MAbs described in EP-A1-0 388 914. The fusion proteins according to the invention particularly preferably contain the humanized MAb fragment with the $V_L$ and $V_H$ genes shown in Table 3, L is a linker and preferably contains a hinge region of an immunoglobulin which is linked via a peptide sequence to the N-terminus of the mature enzyme, and β-Gluc is the complete amino-acid sequence of human β-glucuronidase or, in the relevant gene constructs, the complete cDNA (Oshima A. et al., Proc. Natl. Acad. Sci. USA 84, (1987) 685–689).

In these fusion proteins, the huTuMAb ensures the specific localization of tumors, L connects huTuMAb to β-Gluc in such a way that the specific properties of the two fusion partners are not impaired, and β-Gluc activates a suitable prodrug compound by elimination of glucuronic acid, where a virtually autologous system for use in humans is provided by the humanized or human fusion partners.

Furthermore preferred are constructs with a $CH_1$ exon and a hinge exon in the antibody part, and particularly preferred constructs are those in which these parts derive from a human IgG3 C gene. Most preferred are constructs, as described in Example 16, where the corresponding light chain of the humanized TuMab is co-expressed in order, in this way, to obtain an huTuMAb portion which is as similar as possible to the original TuMAb in the binding properties.

Furthermore, it has been found that a chemical modification of the fusion proteins, in particular partial or complete oxidation of the carbohydrate structures, preferably with subsequent reductive amination, results in an increased half-life. Enzymatic treatment of the fusion proteins according to the invention with alkaline phosphatase from, for example, bovine intestine or *E. coli* has in general not resulted in a significant increase in the half-life.

Accordingly, in another embodiment, the fusion proteins according to the invention are chemically modified in order to achieve an increased half-life and thus an improved localization of tumors. The fusion proteins are preferably treated with an oxidizing agent, for example periodate, which generally results in partial or complete cleavage of the carbohydrate rings and thus in an alteration in the carbohydrate structure. This alteration generally results in an increased half-life. It is furthermore advantageous to derivatize, in a second reaction step, existing aldehyde groups, for example by reductive amination. The partial or complete destruction of the aldehyde groups generally results in a reduction in possible side reactions with, for example, plasma proteins. Accordingly, it is advantageous for the fusion proteins according to the invention to be oxidized in a first reaction step, for example with periodate, and to be reductively aminated in a second reaction step, for example with ethanolamine and cyanoborohydride.

The process according to the invention for preparing a compound of the formula I, which can be degraded by glycosidase, in which $R^1$ is a methyl, benzyl or 2-thienyl group, $R^2$ is a hydrogen atom, $R^3$ is a hyroxyl, amino or dimethylamino group, $R^4$ is a hydrogen atom or a methyl group, $R^5$ is a hydrogen atom, a hydroxyl group, an amino or acetylamino group, $R^6$ is a hydroxyl group or an amino group, $R^7$ is a hydrogen atom, and $R^8$ is a methyl or hydroxymethyl group or a carboxyl group or an acyl protective group which is bonded via a methyleneoxy group, or a benzyloxycarbonyl group, where an acyl protective group means an acetyl, mono-, di- or trihalogenoaceyl group with halogen meaning fluorine or chlorine, comprises reacting, in the presence of a promoter and, where appropriate, of an acid trap or drying agent in a solvent at −50° C. to 60° C., an etoposide compound of the formula VI

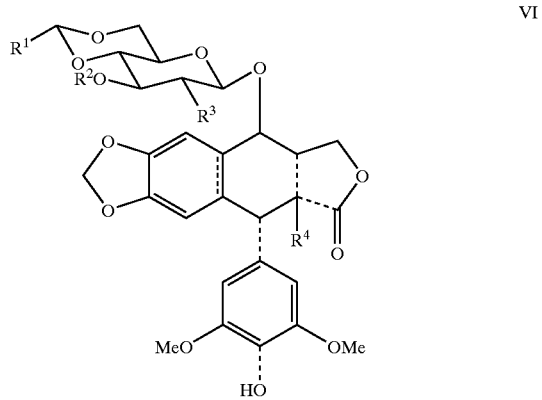

in which

R is a methyl, benzyl or 2-thienyl group, $R^2$ is a hydrogen atom, an acyl or a tri-$C_1$–$C_4$-alkylsilyl protective group, $R^3$ is a hydroxyl group, an acyl or tri-$C_1$–$C_4$-alkylsilyl protective group which is bonded via oxygen, or acetylamino, benzyloxycarbonylamino or dimethylamino group, and $R^4$ is a hydrogen atom or a methyl group, with a carbohydrate component of the formula VII

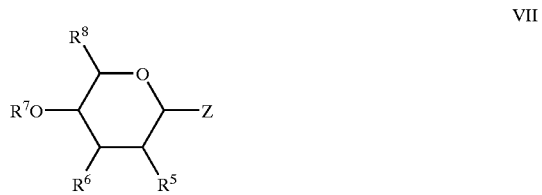

in which $R^5$ is a hydrogen atom, a hydroxyl group, an acyl protective group which is bonded via an oxygen atom, or benzyloxycarbonylamino, azido or acetylamino group, $R^6$ is an acyl protective group which is bonded via an oxygen atom, or a benzyloxycarbonylamino or azido group, $R^7$ is an acyl protective group, $R^8$ is a methyl group, methyleneoxy-acyl protective group or a benzyloxycarbonyl group and Z is a halogen atom, preferably fluorine, chlorine or bromine, a hydroxyl group, a tri-$C_1$–$C_4$-alkylsilyloxy group, or an acyl protective group which is bonded via an oxygen atom, where the acyl protective group is an acetyl, mono-, di- or trihalogeno-acetyl group, preferably with the halogen atom being fluorine or chlorine, to give a 4'-O-glycosyl-etoposide derivative of the formula I in which all the radicals $R^1$ to $R^8$ retain their meaning as defined above, and eliminating the protective groups present in these compounds by hydrogenolysis or hydrolysis, and, where appropriate, converting by means of reductive alkylation one of the resulting compounds containing amino groups into another compound of the formula I containing dimethylamino groups.

The specific procedure for this is as follows: the glycosidation of etoposide derivatives of the formula VI is carried out using functionalized carbohydrate units of the formula VII which are typically protected with acyl protective groups on the O-2, O-3, O-4 and, where appropriate, O-6 atoms. Preferred acyl protective groups are acetyl, chloroacetyl or trifluoroacetyl groups. In the case of amino sugars, the amino group is protected temporarily with the benzyloxycarbonyl group or permanently with an acetyl group. It is likewise possible to use azido sugars because they can be converted straightforwardly into amino sugars by hydrogenolysis. The carbohydrate components must be suitably functionalized at the anomeric center. Used for.this purpose are glycosyl halides, such as fluorides, chlorides or bromides, which can be prepared starting from 1-O-acyl derivatives, for example using HF, HCl, HBr or $TiBr_4$. The glycosidation components which carry an O-acyl group or a hydroxyl group on the anomeric center are prepared by processes customary in carbohydrate chemistry.

The glycosidation of etoposides of the formula VI with carbohydrate units of the formula VII is carried out in the presence of a promoter. The promoter used when glycosyl fluorides and the 1-hydroxy or 1-acetyloxy analogs thereof are employed is $BF_3x$ ether or tri-$C_1$-$C_4$-alkylsilyl trifluoromethanesulfonate. The promoters used in the case of glycosyl chlorides or bromides are salts of silver or of mercury.

The glycosidation is carried out in an aprotic organic solvent such as acetone, ethyl acetate, ether, toluene, dichloromethane or dichloroethane or mixtures thereof. In order to trap the acid or water produced in the reaction, where appropriate, acid traps or drying agents such as molecular sieves or magnesium sulfate are added. The reaction temperature is in the range from −50° C. to 0° C. when glycosyl fluorides and the 1-hydroxy analogs are employed and at 0° C. to 60° C. when glycosyl chlorides or bromides are employed. The glycosyl etoposides produced in the reaction are deblocked by the following processes: the acyl protective groups are removed by methanolysis catalyzed by zinc (II) salts or with alkaline ion exchangers in methanol, ethanol or mixtures thereof with chloroform, dichloromethane or ether. The benzyl or benzyloxycarbonyl groups or azido groups are eliminated by hydrogenolysis with palladium on carbon or palladium/barium sulfate or, in the case of the azido group, converted into amino group. The compounds of the formula I containing amino sugars can additionally be converted into dimethylamino derivatives by reductive alkylation with formaldehyde/sodium cyanoborohydride.

To prepare the functionalized tumor-specific enzyme conjugates of the invention, the spacer (Sp) can be linked via an amino group to an enzyme and to the antibody or the biomolecule via an HS group which has been introduced or generated by cleavage of the disulfide linkage, or nucleic acid sequences which code for the parts A, Sp and E are covalently linked with the aid of molecular biological methods to result in a fusion gene, and A—Sp—E is prepared by genetic engineering processes.

The coupling is carried out by processes described in the literature (A. H. Blair and T. I. Ghose, (1983) J. Immunolog. Methods 59, 129–143; T. I. Ghose et al. (1983) Methods in Enzymology, Vol. 93, 280–333). This entails initial functionalization of the enzyme via its amino group using succinimidyl N-maleimido-alkylidene-, cycloalkylidene- or arylene-1-carboxylate, where the double bond of the maleimido group enters into a reaction with the HS group of the functionalized antibody, fragment thereof or the biomolecules, with the formation of a thioether functionality.

Preparing the functionalized tumor-specific enzyme conjugates by genetic engineering processes can be carried out in a variety of ways:

A) A restriction cleavage site A is introduced by specific mutagenesis at the 3' end of the $C_H1$ exon in the gene of the heavy chain of the immunoglobulin. The same restriction cleavage site A is generated at the 5' end of the oligonucleotide which codes for the oligopeptide which acts as spacer. Both restriction cleavage sites A are sited in such a way that the immunoglobulin gene can be linked to the oligonucleotide via the restriction cleavage site A without disturbing the reading frame.

A restriction cleavage site B is generated at the 3' end of the oligonucleotide. This restriction cleavage site B is introduced at the site in the gene which codes for the enzyme at which the nucleic acid sequence coding for the mature protein starts. The enzyme gene is then linked via the restriction cleavage site B to the immunoglobulin gene-linked construct. The restriction cleavage sites B are sited such that the reading frame is not disturbed on linkage. The fusion gene composed of the DNA for the heavy chains of the immunoglobulin $V_H$ and $C_H1$ linker enzyme is cloned into an expression plasmid which is suitable for expression in the eukaryotic cells and carries a selection marker.

The expression plasmid with the fusion gene is transfected together with an expression plasmid which carries the gene for the light chain belonging to the antibody into eukaryotic cells (for example myeloma cells). Selection with suitable antibiotics is carried out to isolate cell clones which contain the plasmids with the fusion gene and the gene for the light chains (transfectomas). Suitable detection methods (BioDot; ELISA) are used to identify those transfectomas which secrete the fusion protein of the formula A—Sp—E composed of the MAb Fab part, linker polypeptide and enzyme.

B) A restriction cleavage site A is introduced at the 3' end of the hinge exon of the gene for the heavy chains of the immunoglobulin. The restriction cleavage site A is introduced at the site in the enzyme gene at which the nucleotide sequence coding for the mature protein starts. The gene fragment of the heavy chains of the immunoglobulin with the $V_H$, $C_H1$ and hinge exons is linked via the restriction cleavage site A to the enzyme gene.

The restriction sites A are sited such that the reading frame is not disturbed on linkage. The hinge part of the antibody functions as the polypeptide spacer in this construction. The fusion gene composed of $V_H$, $C_H1$ hinge and enzyme gene is cloned into an expression plasmid which is suitable for expression in eukaryotic cells and carries a selection marker. The expression plasmid with the.fusion gene is transfected together with an expression plasmid which contains the light-chain gene belonging to the antibody into eukaryotic expression cells. Selection with a suitable antibiotic is followed by identification of transfectoma clones which contain the expression plasmids. Suitable detection methods (BioDot, ELISA) are used to identify those transfectoma clones which secrete the fusion protein of the formula II composed of antibody andenzyme.

It is possible to use for the preparation of the antibody-enzyme conjugates the monoclonal antibodies described in EP-A-0141079, preferably the antibodies 431/26, 250/183, 704/152 and 494/32. The specificity of the antibodies for tumor-associated antigens has already been demonstrated on animals and humans by means of immunoscintigraphy and immunohistochemistry.

The nucleotide sequence of the V genes of these monoclonal antibodies is described in German Patent Application DE-A-39099799.4.

To prepare the tumor-specific enzyme conjugates, it is possible for the enzymes which are mentioned hereinafter and from the identified source to be purified by the indicated literature procedures:

α-galactosidase from human liver, Dean, K. G. and Sweeley, C. C. (1979) J. Biol. Chem. 254, 9994–10000

β-glucuronidase from human liver, Ho, K. J. (1985) Biochem. Biophys. Acta 827, 197–206

α-L-fucosidase from human liver, Dawson, G., Tsay, G. (1977) Arch. Biochem. Biophys. 184, 12–23

α-mannosidase from human liver, Grabowski, G. A., Ikonne, J. U., Desnick, R. J. (1980) Enzyme 25, 13–25

β-mannosidase from human placenta, Noeske, C., Mersmann, G. (1983) Hoppe-Seyler's Z. Physiol. Chem. 364, 1645–1651

α-glucosidase from human gastrointestinal mucosa, Asp, N.-G., Gudmand-Hoeyer, E., Christiansen, P. M., Dahlquist, A. (1974) Scand. J. Clin. Lab. Invest. 33, 239–245

β-glucosidase from human liver, Daniels, L. B., Coyle, P. J., Chiao, Y.-B, Glew, R. H. (1981) J. Biol. Chem. 256, 13004–13013

β-glucocerebrosidase from human placenta, Furbish, F. S., Blair, H. E., Shiloach, J., Pentcheu, P. G., Brady, R. O. (1977) Proc. Natl. Acad. Sci. USA 74, 3560–3563

α-N-acetylglucosaminidase from human placenta, Rohrborn, W., von Figura, K. (1978) Hoppe-Seyler's Z. Physiol. Chem. 359, 1353–1362

β-N-acetylglucosaminidase from human amniotic membrane, Orlacchio, A., Emiliani, C., Di Renzo, G. C., Cosmi, E. V. (1986) Clin. Chim. Acta 159, 279–289

α-N-acetylgalactosaminidase according to Salvayre, R., Negre, A., Maret, A., Douste-Blazy, L. (1984) Pathol. Biol. (Paris) 32, 269–284.

The glycolytic activity of the functionalized tumor-specific enzymes was determined in comparative investigations with p-nitrophenyl glycosides at the particular pH optimum.

To test the efficacy of a combined sequential use, transplanted mice were given the functionalized enzyme, then, after waiting until the plasma level of the enzyme had fallen virtually to zero, the glycosyletoposide was given and it was observed whether growth stopped and regression occurred.

Figure 1:
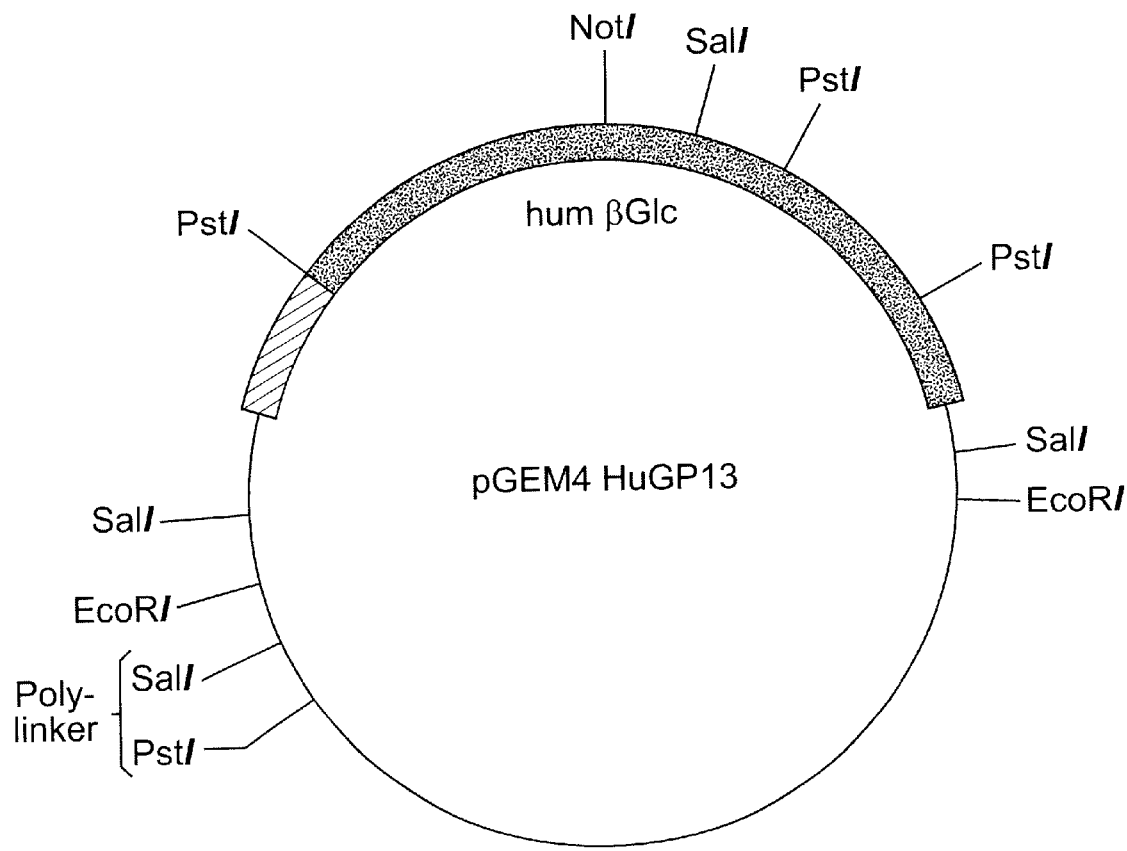
FIG. 1: Restriction map of plasmid pGEM4-HUGP13.

EXAMPLE 1
Preparation of the Glycosylation Component.

Benzyl D-glucuronate (Compound 1)

Benzyl bromide (4.89 g, 28.59 mmol) was added to a solution of sodium D-glucuronate (5 g, 23.13 mmol) in DMF (300 ml). The reaction mixture was stirred at 40° C. for 2 h and then at 80° C. for 16 h and evaporated in vacuo. The residue was purified by column chromatography on silica gel (130 g) with 80:20:1 chloroform/methanol/water. Yield: 4.87 g (74%). The title compound was characterized by $^{13}$C NMR.

Benzyl 1,2,3,4-tetra-O-Chloroacetyl-α and β-D-Glucuronate (Compound 2a and 2b)

Benzyl D-glucuronate (3.80 g, 13.36 mmol) was suspended in dichloromethane (200 ml). Chloroacetyl chloride (7.90 g, 69.94 mmol) was added and then the mixture was cooled to −30° C., and pyridine (4.33 g, 54.74 mmol) dissolved in dichloromethane (50 ml) was added. The reaction mixture was stirred at −30° C. for 16 h and then chloroacetyl chloride (7.90 g) and pyridine (4.33 g) were added. The mixture was stirred for 16 h and then cold dichloromethane (150 ml) was added and the mixture was washed with 5% strength sodium citrate buffer (pH 5, 60 ml×2) and ice-water (50 ml×2). The resulting product (7.92 g), which contained about 30% benzyl 2,3,4-tri-O-chloroacetyl-α, β-D-glucuronate in addition to the title compound, was used without further purification steps in the next stage.

Benzyl 2,3,4-tri-O-Chloroacetyl-α, β-D-Glucuronate (Compound 3a, 3b)

The crude product (7.92 g) of compounds 2a/2b was dissolved in 3:1 methanol/chloroform (320 ml), and aminated silica gel (11.09 g) was added. The reaction mixture was stirred at room temperature for 6 h and filtered. The filtrate was evaporated and then the residue was purified by chromatography on silica gel (220 g) with 2:1 petroleum ether/ethyl acetate.

Yield: 4.94 g (72% based on compounds 2a/2b).

Benzyl 1-Deoxy-1-fluoro-α-D-glucuronate (Compound 4)

Sodium 1-deoxy-1-fluoro-α-D-glucuronate (6.22 g, 28.51 mmol) was suspended in DMF (350 ml), and benzyl bromide (4.89 g, 28.59 mmol) was added. The reaction mixture was stirred at 60° C. for 24 h and then evaporated. The residue was dissolved in 3:1 chloroform/methanol, and magnesium sulfate (12 g) was added. The suspension was stirred for 2 h and then filtered, and the filtrate was evaporated. The residue was purified by column chromatography on silica gel (160 g) with 4:1 dichloromethane/acetone.

Yield: 5.95 g (73%).

Benzyl 1-Deoxy-1-fluoro-2,3,4-tri-O-α-D-glucuronate (Compound 5)

Compound 4 (5.0 g, 17.46 mmol) was suspended in dichloromethane (120 ml) and, at 0° C., benzyl bromide (9.85 g, 57.61 mmol) and silver oxide (11.2 g) were added. The reaction mixture was stirred at 0° C. for 5 h and then at room temperature for 28 h. The reaction mixture was filtered, and the filtrate was evaporated in vacuo. The residue was purified by chromatography on silica gel (240 g) with 3:1 petroleum ether/ethyl acetate.

Yield: 6.60 g (68%).

Benzyl 1-Deoxy-1-fluoro-2,3,4-tri-O-chloroacetyl-α-D-glucuronate (Compound 6)

Compound 4 (5.0 g, 17.46 mmol) was suspended in dichloromethane (260 ml) and, at −30° C., chloroacetyl chloride (9.86 g, 87.30 mmol) was added. After addition of 10:1 dichloromethane/pyridine (100 ml), the reaction mixture was stirred at −30° C. for 18 h. Cold dichloromethane (80 ml) was added to the mixture, which was washed with sodium citrate buffer (pH 5.0, 80 ml×3) and then with water. The organic phase was dried over sodium sulfate and evaporated. The residue was purified by column chromatography on silica gel (260 g) with 5:1 petroleum ether/ethyl acetate.

Yield: 7.58 g (92%).

2,3,4,6-tetra-O-Chloroacetyl-α-D-galactopyranosyl Fluoride (Compound 7)

α-D-galactopyranosyl fluoride (2.30 g, 12.62 mmol) was dissolved in dry dichloromethane (100 ml) and, at −25° C., chloroacetyl chloride (9.0 g, 79.68 mmol) and 1:1 dichloromethane/triethylamine (55 ml) were added. The reaction mixture was stirred for 16 h and then chloroacetyl chloride (9.0 g) and 1:1 dichloromethane/triethylamine (55 ml) were added. The reaction mixture was stirred for a further 24 h and then washed with sodium citrate buffer (pH 5.0, 50 ml×3) and then with water. The organic phase was dried (sodium sulfate) and evaporated in vacuo. The residue was purified by column chromatography on silica gel (300 g) with 40:8:1 dichloromethane/petroleum ether/ethyl acetate.

Yield: 5.19 g (82%); $[\alpha]_D$+64.20 (c=1, dichloromethane).

2,3,4,6-tetra-O-Benzyl-α-D-galactopyranosyl Fluoride (Compound 8)

α-D-galactopyranosyl fluoride (2.30 g, 12.62 mmol) was dissolved in dry DMF (40 ml) and, at −20° C., benzyl bromide (12.95 g, 75.72 mmol) and silver oxide (10 g) were added. The reaction mixture was stirred at −20° C. for 5 h and then at room temperature for 24 h. The salts were then filtered off and the filtrate was evaporated in vacuo. The residue was purified by column chromatography on silica gel (350 g) with 15:1 petroleum ether/ethyl acetate.

Yield: 5.20 g (76%).

EXAMPLE 2
Glycoside Synthesis.

4'-0-Demethyl-4-O-(2,3-di-O-chloroacetyl-4,6,0-ethylidene-3-D-glucopyranosyl)-4-epi-podophyllotoxin (Compound 9)

4'-O-Benzyloxycarbonyl-4-O-demethyl-4-O-(2,3-di-O-chloro-acetyl-4,6-O-ethylidene-α-D-glucopyranosyl)-4-epi-podophyllotoxin (10 g, 11.42 mmol) was hydrogenated in 2:1 ethyl acetate/methanol (200 ml) in the presence of 10% Pd/C (5.0 g) for 2 h. The reaction mixture was filtered, and the filtrate was evaporated in vacuo. The residue was filtered through a layer of silica gel (50 g). The resulting product was crystallized with methanol/ethyl acetate.

Yield: 7.50 g (88.6%); melting point 201–203° C.; [alpha]$_D$−73.4° (c=1, chloroform).

Benzyl 4'-O-Demethyl-4-O-(di-O-chloroacetyl-4,6-O-Ethylidene-β-D-glucopyranosyl)-4-epi-4'-O-(2,3,4-tri-O-benzyl-β-D-glucopyranosyl)-uronate-podophyllotoxin (Compound 9)

Benzyl 1-fluoroglucuronate (compound 5, 4.23 g, 7.60 mmol) and 2", 3"-di-O-chloroacetyl-etoposide (compound 9, 5.63 g, 7.60 mmol) were dissolved in dichloromethane (220 ml), and 4 Å molecular sieves (10 g) were added. BF$_3$-ether (2.5 ml) was added at −40° C. to the reaction mixture, which was then stirred at −30° C. for 20 h. Triethylamine (7.0 ml) was added and then the mixture was filtered. The filtrate was washed with citrate buffer (pH 5, 80 ml×3) and water (120 ml×3), dried (sodium sulfate) and evaporated in vacuo. The residue was purified by column chromatography on silica gel (360 g) with 5:5:1 dichloromethane/petroleum ether/acetone.

Yield: 6.49 g (67%).

4'-O-Demethyl-4-O-(di-O-chloroacetyl-4,6-O-ethylidene-β-D-glucopyranosyl)-4-epi-4'-O-(2,3,4,6-tetra-O-benzyl-α- and β-D-Glactopyranosyl)-podophyllotoxin (Compound 10a and 10b)

Tetra-O-benzyl-galactopyranosyl fluoride (compound 8, 3.60 g, 6.65 mmol) and etoposide derivative (compound 9, 4.93 g, 6.65 mmol) were dissolved in dichloromethane (250 ml). 4 Å molecular sieves (7.2 g) were added and then the reaction mixture was cooled to −40° C., and 30% strength BF$_3$-ether (2.2 ml) was added dropwise. The mixture was stirred at −30° C. for 20 h and then, after addition of triethylamine (5.5 ml), filtered. The filtrate was washed with citrate buffer (75 ml×3, pH 5) and water (70 ml×2), dried over sodium sulfate and evaporated. The residue was prepurified by column chromatography on silica gel (370 g) with 5:5:1 petroleum ether/dichloromethane/acetone. Further separation by column chromatography provided the title compounds 10a (α-glycoside: 4.36 g (52%)) and 10b (β-glycoside: 1.42 g (17%)).

EXAMPLE 3
Deblocking Reaction for Glycosyl Etoposides.

Benzyl 4'-O-Demethyl-4-epi-4-O-(4,6-O-ethylidene-β-D-glucopyranosyl)-4'-O-(2,3,4-tri-O-benzyl-β-D-glucopyranosyl)-uronate Podophyllotoxin (Compound 11)

Glucuronide derivative (compound 9, 4.56 g, 3.57 mmol) was dissolved in 4:1 methanol/chloroform (120 ml), and DOWEX 1×8 (6.2 g) was added. The reaction mixture was stirred at room temperature for 3 h and then filtered. Chloroform (150 ml) was added to the filtrate, which was then stirred with magnesium sulfate (10 g). The salts were filtered off and then the filtrate was evaporated in vacuo. The residue was purified by column chromatography on 200 g of silica gel with 5:2:1 dichloromethane/petroleum ether/acetone.

Yield: 3.29 g (82%).

4'-O-Demethyl-4-epi-4-O-(4,6-O-ethylidene-β-D-glucopyranosyl)-4'-O-(β-D-glucopyranosyl)-uronic Acid Podophyllotoxin (Compound 12)

Deacylated glucuronide derivative (compound 11, 3.62 g, 3.22 mmol) was dissolved in 4:1 methanol/ethyl acetate (180 ml) and hydrogenated in the presence of 10% Pd/C (2.76 g) for 20 h. The catalyst was filtered off and then the filtrate was evaporated in vacuo. The residue was purified by column chromatography on RP-18 silica gel using methanol/hexane (gradient).

Yield: 1.82 g (74%).

4'-O-Demethyl-4-epi-4-O-(4,6-O-ethylidene-β-D-gluco-pyranosyl)-4'-O-(2,3,4,6-tetra-O-benzyl-α-D-galacto-pyranosyl)-podophyllotoxin (Compound 13)

Podophyllotoxin galactopyranoside (compound 10a, 3.0 g, 2.37 mmol) was dissolved in 3:1 methanol/chloroform, and DOWEX 1×8 was added. The reaction mixture was stirred at room temperature for 3 h and filtered. The filtrate was evaporated in vacuo. The residue was dissolved in chloroform and washed with phosphate buffer (pH 7, 30 ml×3) and then with water. The organic phase was dried over sodium sulfate and evaporated. The residue was purified by column chromatography on silica gel (85 g) with 5:3:1 dichloromethane/petroleum ether/acetone.

Yield: 2.27 g (86%).

4'-O-Demethyl-4-epi-4'-O-(α-D-galactopyranosyl)-4-O-(4,6-O-ethylidene-β-D-glucopyranosyl)-podophyllotoxin (Compound 14)

Deacylated podophyllotoxin galactopyranoside (compound 13, 2.0 g, 1.80 mmol) was dissolved in 3:1 methanol/ethyl acetate and hydrogenated in the presence of 10% Pd/C (2.5 g) for 24 h. The mixture was stirred with magnesium sulfate and filtered. The filtrate was evaporated in vacuo. The residue was purified by column chromatography on RP-18 silica gel using methanol/ethyl acetate (gradient).

Yield: 1.37 g (72%).

EXAMPLE 4

Determination of the Enzyme Activity of β-glucuronidase Conjugates.

The β-glucuronidase purified by the above-mentioned procedure was coupled to the antibody/the biomolecule, and the activity of the enzyme and of the conjugate was determined as follows:

500 μl of the enzyme solution to be determined were added to 500 μl of a 2.5 mM p-nitrophenyl β-D-glucuronide solution in 100 mM HEPES (N-2-hydroxyethyl-piperazine-N'-2-ethane-sulfonic acid), pH 5. The assay mixture was incubated at 370 and stopped after 6 min with 300 μl of a 0.4 M glycine solution, pH 10.8. The liberated p-nitrophenol was then determined by measuring the extinction at 405 nm.

Result:

The conjugate showed an only inconsiderable reduction in enzyme activity.

EXAMPLE 5

In Vivo Antitumor Effects of the Glycosyl-etoposide Prodrug System.

30 NMRI nu/nu mice received on day 0 a subcutaneous inoculation of pieces about 5 mm³ in size of CoCa 4 human tumor per animal. After the human tumor tissue had grown in the mice (day 7–14), 5 animals in each of the groups a, b, c received 5×500 μg of Mab BW 494/32-glucuronidase conjugate, d received 5×500 μg of MAb BW 494/32, e received 5×500 μg of glucuronidase and f received 5×500 μl of PBS injected intravenously on 5 consecutive days.

On days 5, 6 and 7 after the end of the MAb BW 494/32-glucuronidase, MAb BW 494/32, glucuronidase or PBS injection, the mice in groups a, d and e received one third of the maximum tolerable dose (MTD) of the glycosyl-etoposide injected intravenously per animal and per day. The mice in group b each received 1/10 of the MTD, and those in group c received 1/20 of the MTD on the same days.

Result:

Groups d and e exhibited a tumor growth which did not differ significantly from that in group f. Groups a, b and c exhibited distinct inhibition of tumor growth, with the effects being most distinct in group a.

Comparable results were received with the MAbs BW 431/26, BW 250/183 in the CoCa4 xenograft system and with the MAB BW 704 in the M21 xenograft system.

EXAMPLE 6 a) Cleavage of 4'-O-α-D-Galactopyranosyl-etoposide With α-Galactosidase (From Green Coffee Beans)

4'-O-α-D-galactopyranosyl-etoposide was dissolved in a concentration of 1 mg/ml in 20 mM sodium phosphate buffer, pH 5, and 0.3 U/ml of α-galactosidase (green coffee beans; Sigma Co.; 1 U=cleavage of 1 μmol of p-nitrophenyl α-D-galactoside per minute at pH 6.5 and 25° C.) was added, and the mixture was incubated at 37° C. The breakdown of 4'-O-α-D-galactopyranosyl-etoposide and the appearance of free etoposide were investigated by HPLC. The half-life was 15 minutes.

b) Cleavage of 4'-O-α-D-Galactopyranosyl-etoposide With α-Galactosidase A (From Human Placenta)

4'-O-α-D-galactopyranosyl-etoposide was dissolved in a concentration of 107 or 10.7 μg/ml in 20 mM sodium phosphate buffer, pH 5, and 0.36 U/ml of α-galactosidase A (isolated from human placenta; 1 U=cleavage of 1 μmol of 4-methumbelli-feryl α-D-galactoside per minute at pH 5 and 37° C.) was added and the mixture was incubated at 37° C. The breakdown of 4'-O-α-D-galacto-pyranosyl-etoposide and the appearance of free etoposide were investigated by HPLC. The half-life was 4 or 7 hours respectively.

EXAMPLE 7

A. Glycosylation of Etoposides.

General Procedure

Molecular sieves (1.4 g), silver carbonate (0.857 g) and silver perchlorate were added at −20° C. to a solution of 2",3"-di-O-chloroacetyl-etoposide (0.67 mmol) and glycosyl halide (bromide or chloride, 1.2 mmol) in dichloromethane (50 ml), and the reaction mixture was stirred with exclusion of light for 60 h. Dichloromethane (50 ml) was added to the mixture, which was then filtered. The filtrate was washed with water and dried over magnesium sulfate. The residue was chromatographed, resulting in the α- and β-O-glycosidically linked compounds.

2",3"-di-O-Chloroacetyl-4'-O-(2,3,4,6-tetra-O-benzyl-α-D-galactopyranosyl)-etoposide The title compound was prepared starting from 2,3,4,6-tetra-O-benzyl-α-D-galactopyranosyl chloride (or bromide) and 2",3"-di-O-chloroacetyl-etoposide by the above-mentioned procedure.

α-glycoside $[\alpha]_D$+11.8° (c=1, chloroform).

2",3"-di-O-Chloroacetyl-4'-O-(2,3,4,6-tetra-O-benzyl-3-D-galactopyranosyl)-etotoside The title compound was prepared starting from 2,3,4,6-tetra-O-benzyl-α-D-galactopyranosyl bromide and 2",3"-di-O-chloroacetyl-etoposide by the above-mentioned procedure.

β-Glycoside $[\alpha]_D$−39.80 (c=1, chloroform).

2",3"-di-O-Chloroacetyl-4'-O-(2,3,4,6-tetra-O-benzyl-α-D-glucopyranosyl)-etoposide The title compound was prepared starting from 2,3,4,6-tetra-O-benzyl-α-D-glucopyranosyl chloride (or bromide) and 2",3"-di-O-chloroacetyl-etoposide by the above-mentioned procedure.

α-glycoside $[\alpha]_D$+16.20 (c=1, chloroform).

2",3"-di-O-Chloroacetyl-4'-O-(2,3,4,6-tetra-O-benzyl-β-D-glucopyranosyl)-etoposide The title compound was prepared starting from 2,3,4,6-tetra-O-benzyl-α-D-glucopyranosyl bromide and 2",3"-di-O-chloroacetyl-etoposide by the above-mentioned procedure.

β-Glycoside $[\alpha]_D$ –44.5° (c=1, chloroform).

2",3"-di-O-Chloroacetyl-4'-O-(2,3,4,6-tetra-O-benzyl-β-D-glucuronyl)-etoposide

The title compound was prepared starting from benzyl 2,3,4-tri-O-benzyl-1-chloro (or -bromo) -1-deoxy-α-D-glucupyranuronate and 2",3'-di-O-chloroacetyl-etoposide by the above-mentioned procedure.

β-Glycoside $[\alpha]_D$ 52.4° (c=1, chloroform).

B. Deblocking of Chloroacetyl Protective Group in Glycosyl-etoposides.

General Procedure

A mixture of a 2",3"-di-O-chloroacetylated glycosyl-etoposide (0.75 mmol) and DOWEX 1×8 ion exchanger (3.0 g) in 3:2 methanol/dichloromethane (200 ml) was stirred at room temperature for 1 h. The resin was filtered off and then the filtrate was washed with phosphate buffer (pH 6), dried (sodium sulfate) and evaporated in vacuo.

The residue was purified by column chromatography. The following compounds were prepared:

4'-O-(2,3,4,6-Tetra-O-benzyl-α-D-galactopyranosyl)-etoposide α-Glycoside $[\alpha]_D$+6.0° (c=1, chloroform)

4'-O-(2,3,4,6-Tetra-O-benzyl-β-D-galactopyranosyl)-etoposide

4'-O-(2,3,4,6-Tetra-O-benzyl-α-D-glucopyranosyl)-etoposide α-Glycoside $[alpha]_D$+14.9° (c=1, chloroform)

14'-O-(2,3,4,6-Tetra-O-benzyl-β-D-glucopyranosyl)-etoposide β-Glycoside $[alpha]_D$53° (c=1, chloroform)

4'-O-(2,3,4,6-Tetra-O-benzyl-β-D-glucuronyl)-etoposide.

Elimination of benzyl protective groups in glycosyletoposides by hydrogenolysis.

General Procedure

A mixture of a benzylated glycosyl-etoposide (0.64= mmol) in glacial acetic acid (10 ml) was hydrogenated in the presence of 10% Pd/C (1.0 g) for 24 h. The catalyst was filtered off and then the filtrate was evaporated in vacuo at about 0° C. The residue was purified by column chromatography on silica gel, resulting in the following glycosyl-etoposides:

4'-O-(α-D-Galactopyranosyl)-etoposide α-Glycoside $[\alpha]_D$+6.2° (c=1, chloroform)

4'-O-(β-D-Galactopyranosyl)-etoposide β-Glycoside $[\alpha]_D$–73.1° (c=1, chloroform)

4'-O-(α-D-Glucopyranosyl)-etoposide

4'-O-(β-D-Glucopyranosyl)-etoposide β-Glycoside $[\alpha]_D$–76.6° (c=0.9, chloroform)

4'-O-(β-D-Glucuronyl)-etoposide.

Additionally, the following examples describe the synthesis by genetic manipulation of a particularly preferred fusion protein of the general formula huTuMAb-L-β-Gluc according to the invention, the derivatization thereof and the demonstration of the ability of the two fusion partners to function.

EXAMPLE 8

The starting material was the plasmid pGEM4-HUGP13 (FIG. 1). pGEM4-HUGP13 contains a cDNA insert which contains the complete coding sequence for the human β-glucuronidase enzyme (Oshima et al. loc. cit.). All the techniques used were taken from Maniatis et al., Molecular Cloning: A Laboratory Manual, Second Edition, Cold Spring Harbor Laboratory Press, Cold Springs Harbor USA (1989).

EXAMPLE 9

Figure 2A:
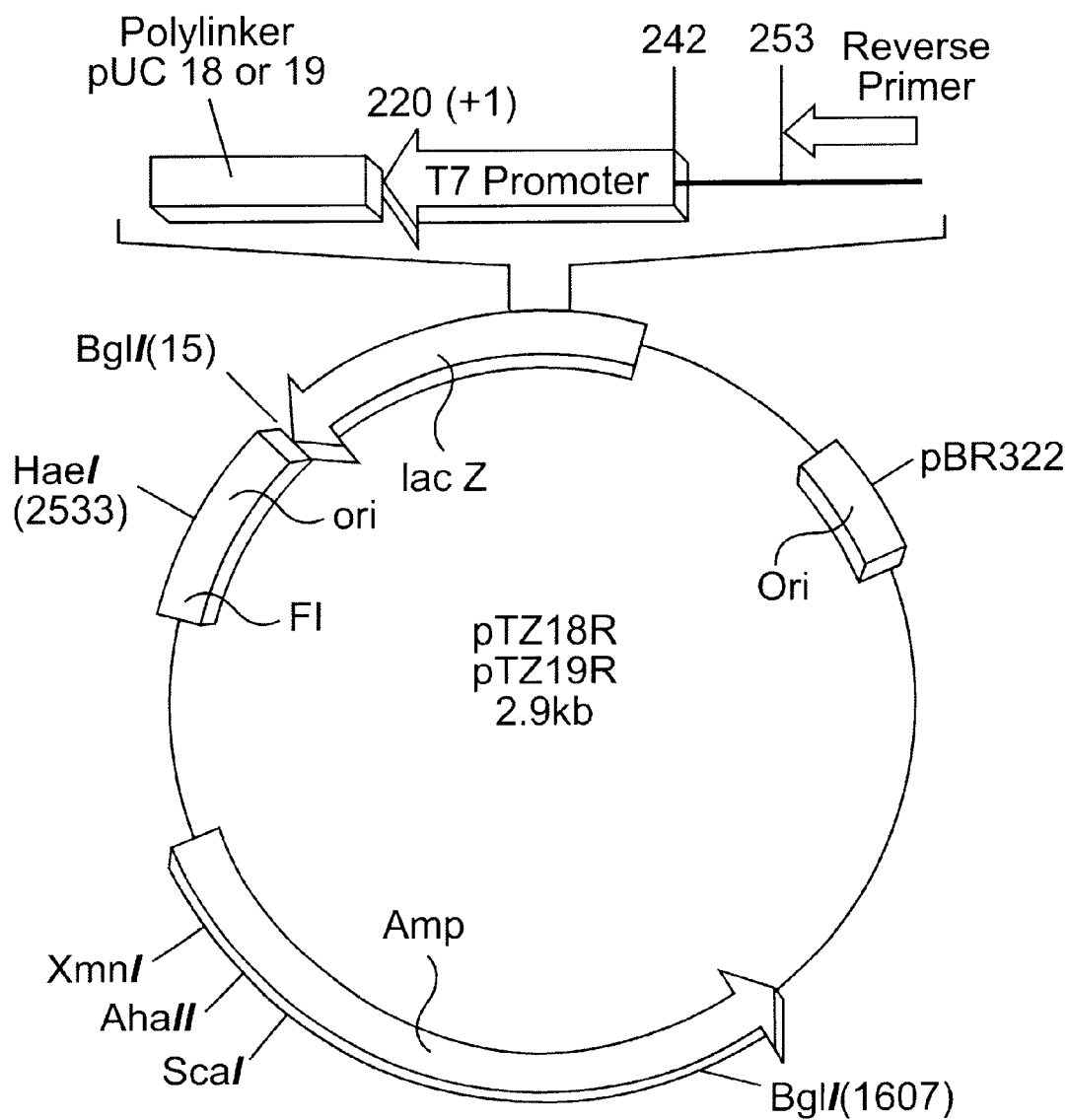
FIG. 2A: Restriction map of plasmid pTZ18R/19R.
Figure 2B:
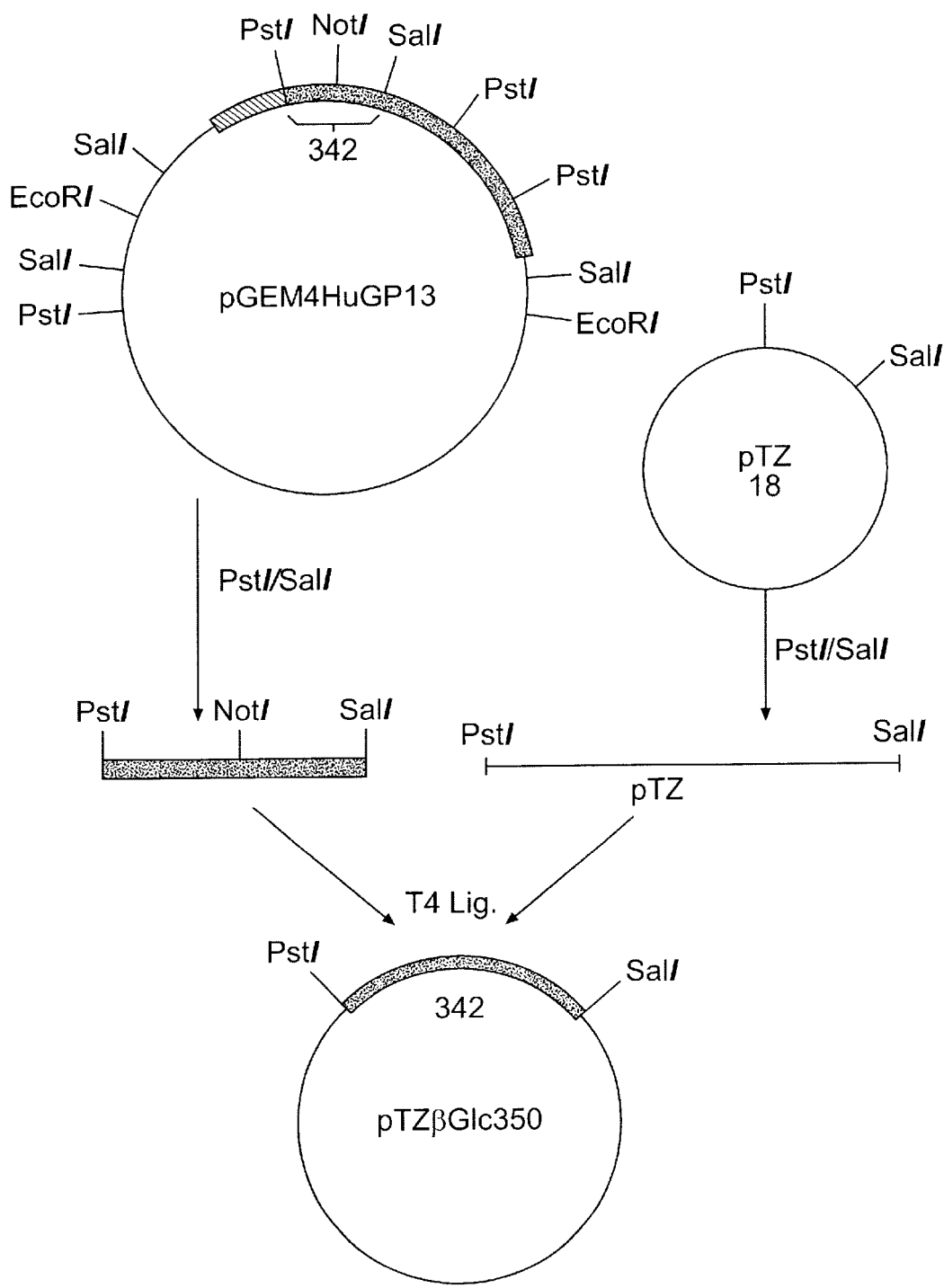
FIG. 2B: Preparation of the plasmid pTZβGlc350.

The plasmid pGEM4-HUGP13 was cut with the restriction endonucleases PstI and SalI, and the 342bp-long PstI/SalI fragment which harbors the NotI restriction cleavage site was isolated. The PstI/SalI fragment was cloned into the PstI/SalI-cleaved vector pTZ (FIG. 2A) and the clone pTZβGlc 350 was isolated (FIG. 2B).

EXAMPLE 10

The plasmid clone PTZβGlc350 was cleaved with PstI, and the double-stranded DNA fragment βGlc linker, which is composed of the oligonucleotides βGlc linker 1 (SEQ. ID No. 1) and βGlc linker 2 (SEQ. ID No. 2) (Table 1) and has cohesive PstI ends, was ligated into the opened PstI cleavage site.

TABLE 1

βGlc Linker 1 (Seq ID No: 1):
    5' GCG GCG GCG GCG GTG CA 3'
βGlc Linker 2 (Seq ID No: 2):
    5' CCG CCG CCG CCG CTG CA 3'

Figure 3:
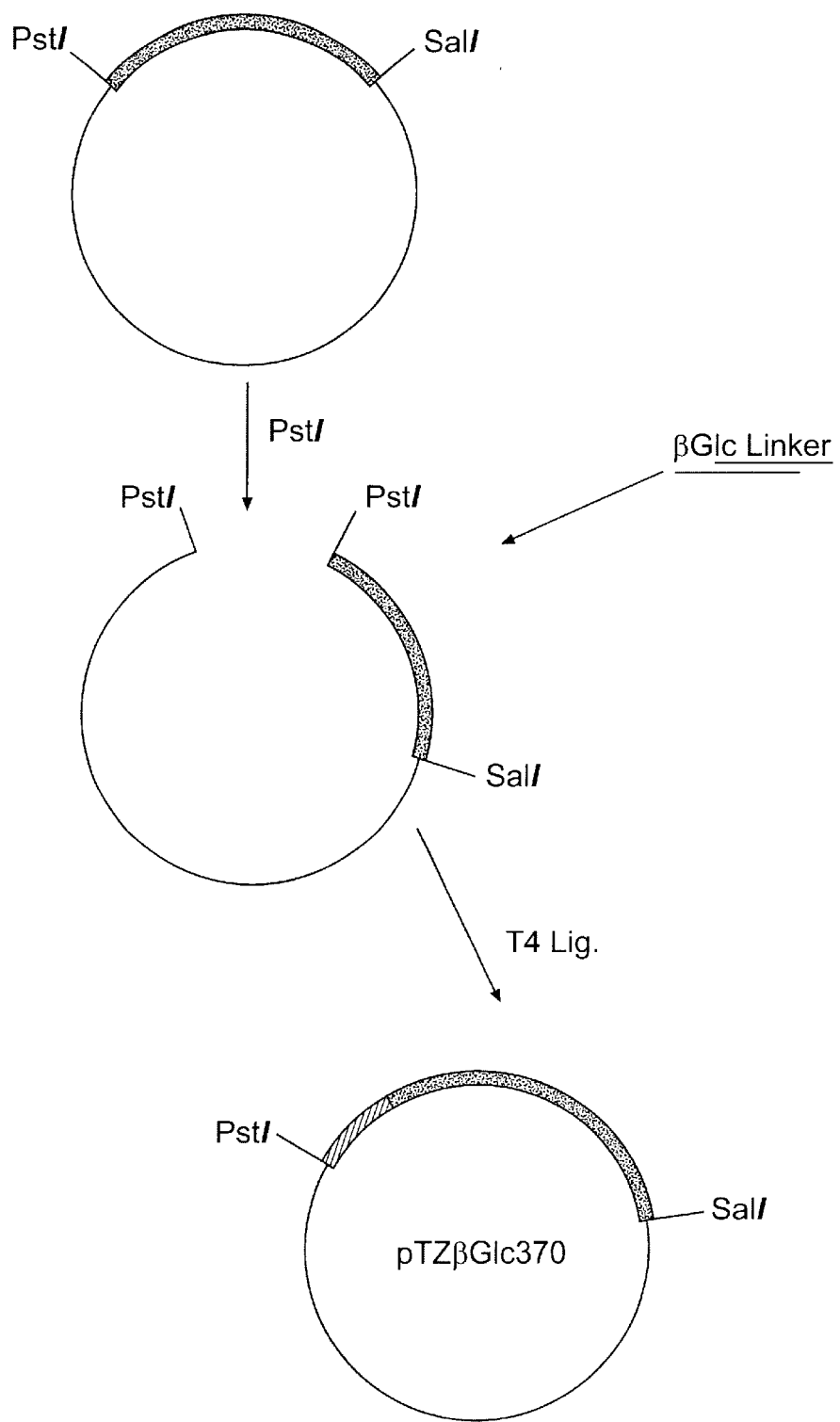
FIG. 3: Preparation of the pTZβGlc370.

The clone pTZβGlc370 in which the β-glucuronidase fragment is extended at its 5' end by oligonucleotide I and which has lost the previously present PstI cleavage site but has aquired instead at its 5' end a new PstI cleavage site was isolated (FIG. 3).

EXAMPLE 11

Figure 4:
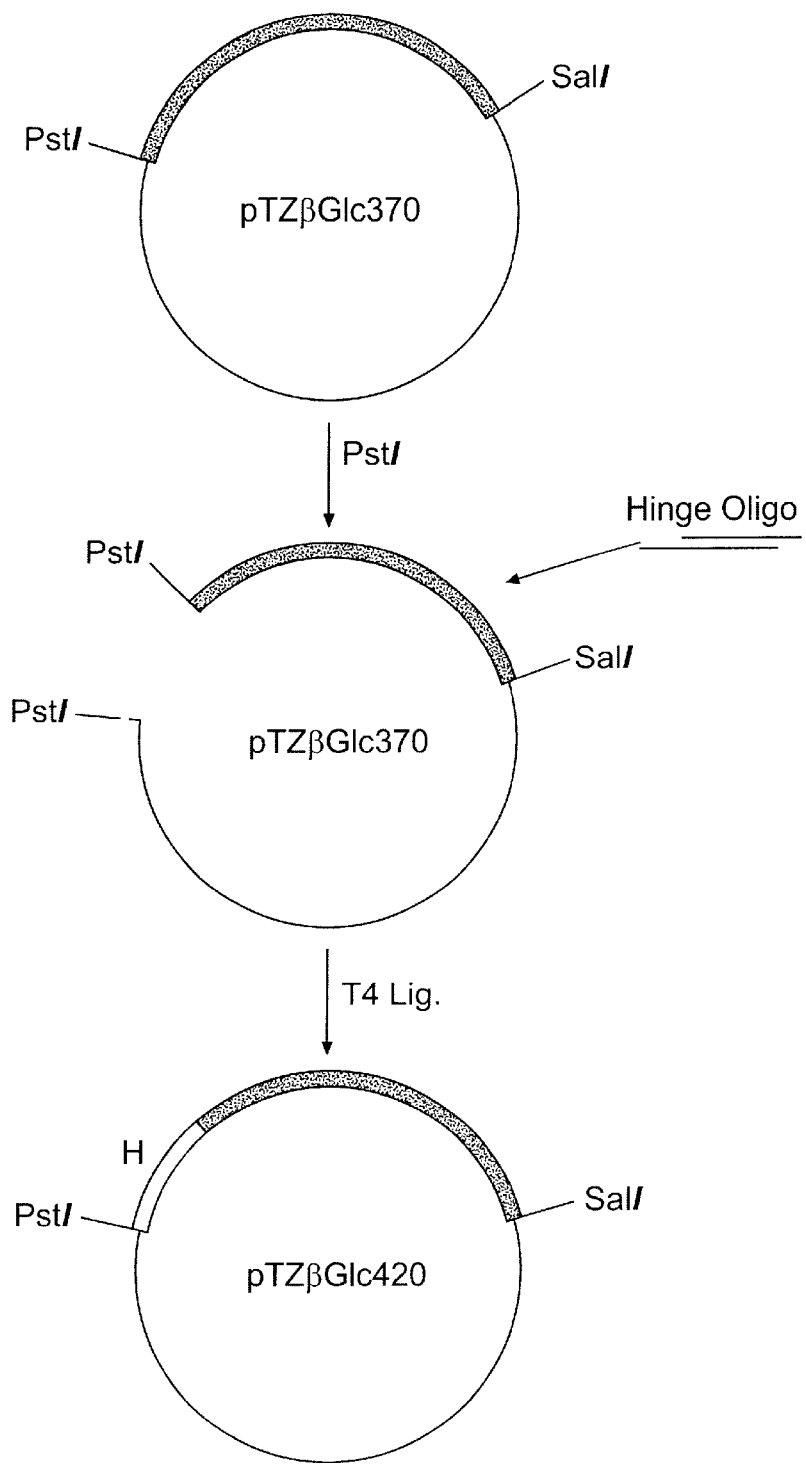
FIG. 4: Preparation of the plasmid pTZβGlc420.
Figure 5:
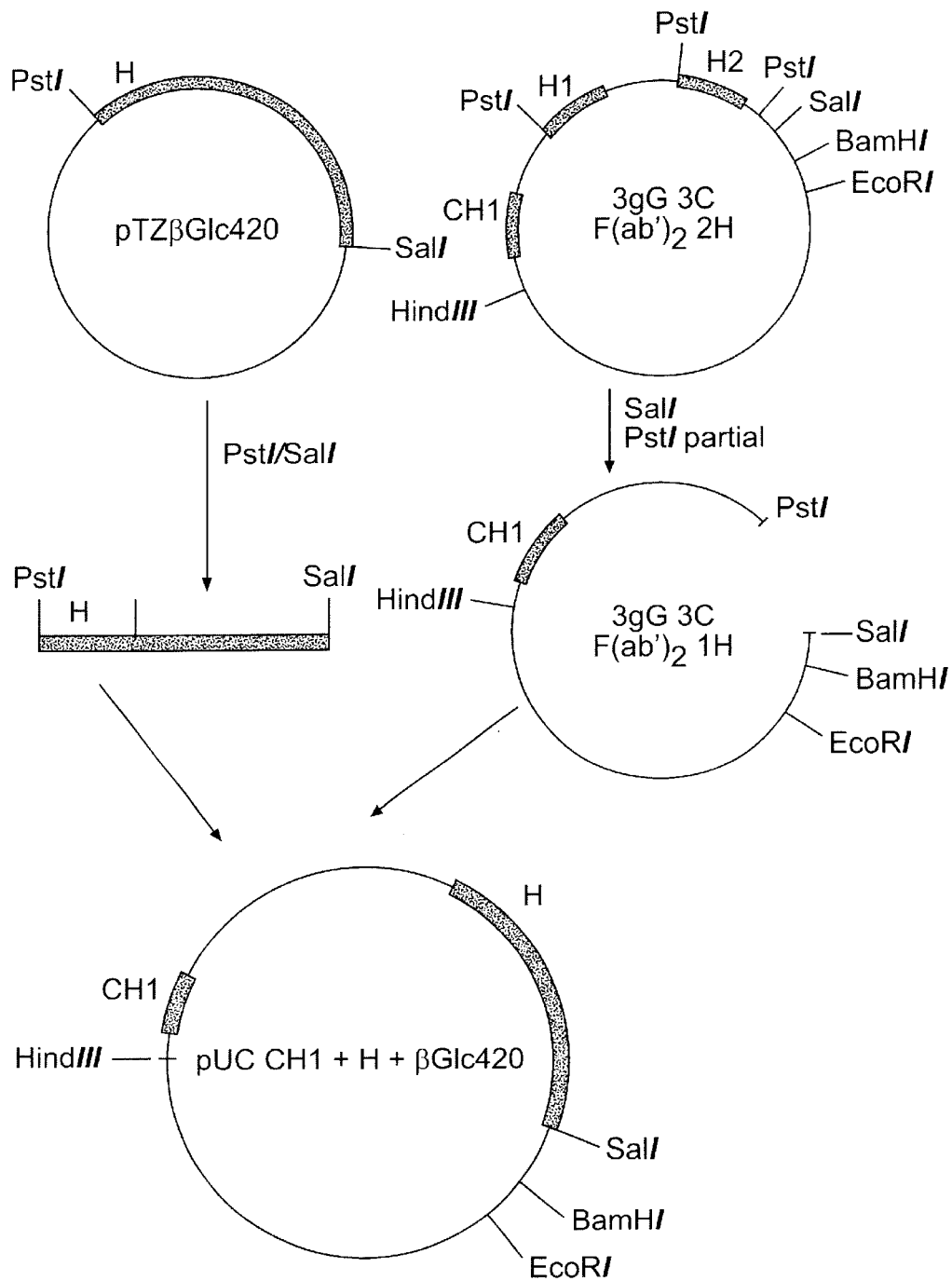
FIG. 5: Preparation of the plasmid pUC CH$_1$+H+ βGlc420.

The plasmid clone pTZβGlc 370 was cleaved with PstI and ligated to the hinge-linker fragment which is composed of the hinge oligonucleotides 1 (SEQ. ID. NO: 3) and 2b (SEQ. ID NO: 4) (Table 2) and which has two cohesive PstI ends. This results in the PstI cleavage site at the 5' end of the βBlc370 fragment being destroyed. The plasmid clone pTZβGlc420 in which the βGlc insert is extended at the 5' end by the linker H was isolated (FIG. 4).

TABLE 2

Hinge 1 Oligo (SEQ. ID No: 3):
5' GAG CCC AAA TCT TGT GAC ACA CCT CCC CCG TGC CCA
CGG TGC CCA GTT GCA 3'
Hinge 2b Oligo (SEQ. ID No: 4):
5' ACT GGG CAC CGT GGG CAC GGG GGA GGT GTG TCA CAA
GAT TTG GGC TCT GCA 3'

EXAMPLE 12

The plasmid pTZβGlc420 was cleaved with PstI and SalI, and the 420 bp insert was isolated. The plasmid IgG3c F(ab')₂ 2H (EP-A2-0 352 761, FIG. 3, ibidem), which contains the $Ch_1$ exon and two hinge exons of a human IgG3 C gene was completely cleaved with SalI and partially cleaved with PstI. The isolated 420 bp insert

EXAMPLE 13

Figure 6:
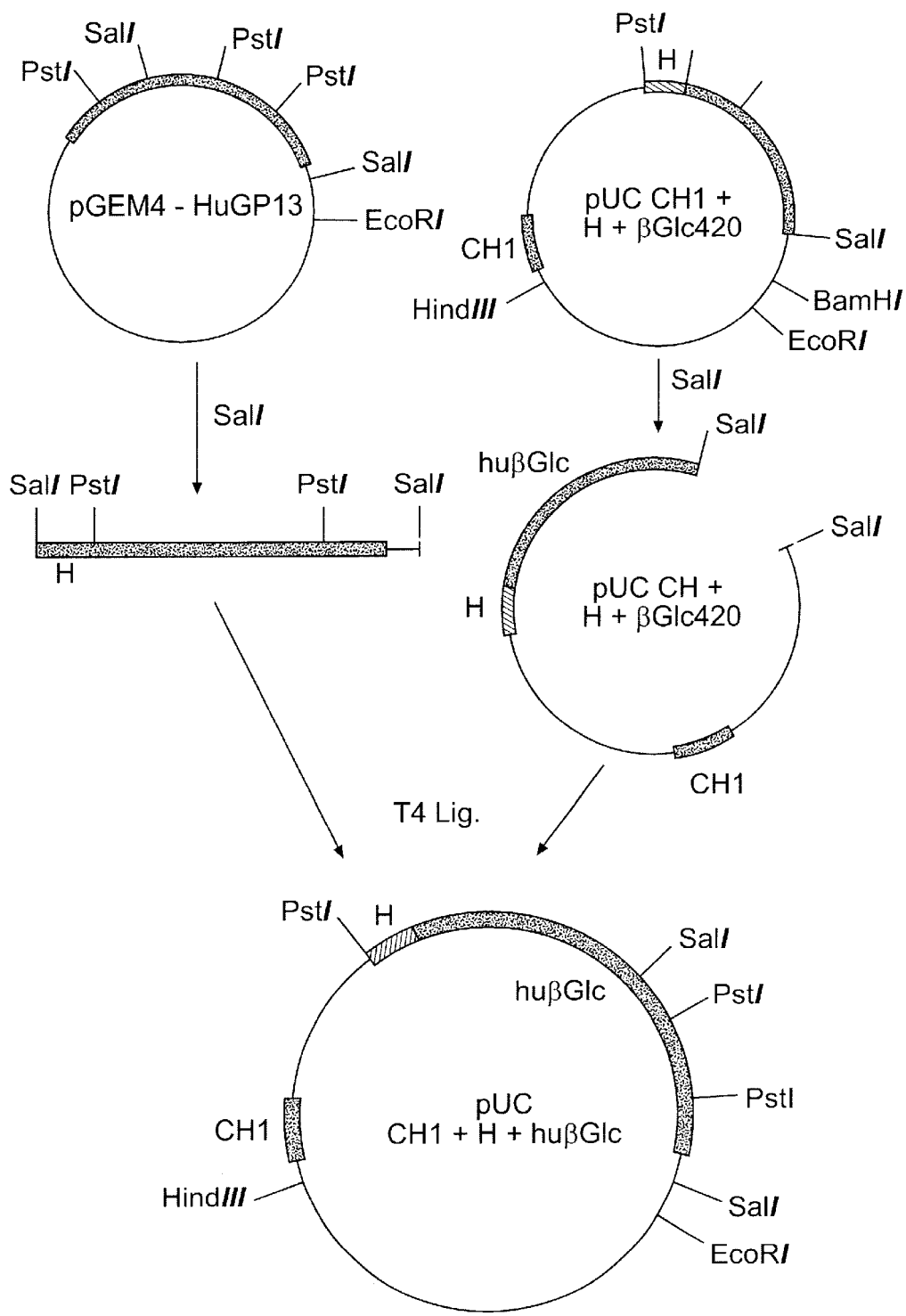
FIG. 6: Preparation of the plasmid pUC CH$_1$+H+huβGlc.

The plasmid pGEM4-HUGP13βGlc was cleaved with SalI, and the 1750bp SalI fragment from the β-gluurinidase cDNA was isolated. The isolated 1750bp SalI fragment was ligated to the SalI-cleaved plasmid pUC $CH_1$+H+βGlc420. The plasmid clone pUC $CH_1$+H+huβGlc which contains a fusion gene composed of a $CH_1$ exon, a hinge exon and a fusion exon between a hinge exon and the human β-glucuronidase cDNA was isloated (FIG. 6).

EXAMPLE 14

Figure 7:
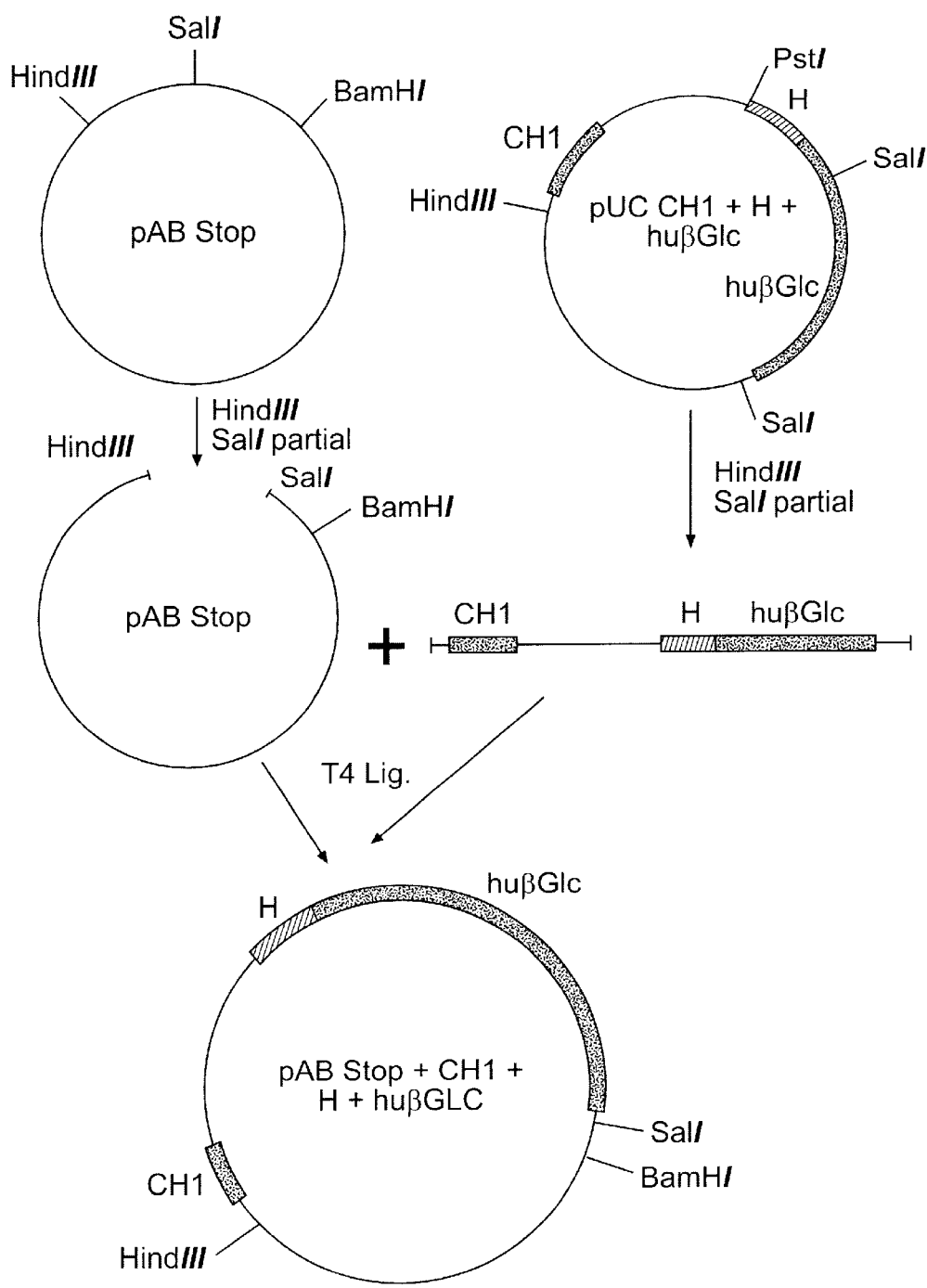
FIG. 7: Preparation of the plasmid pABStop CH$_1$+H+huβGlc.
Figure 9:
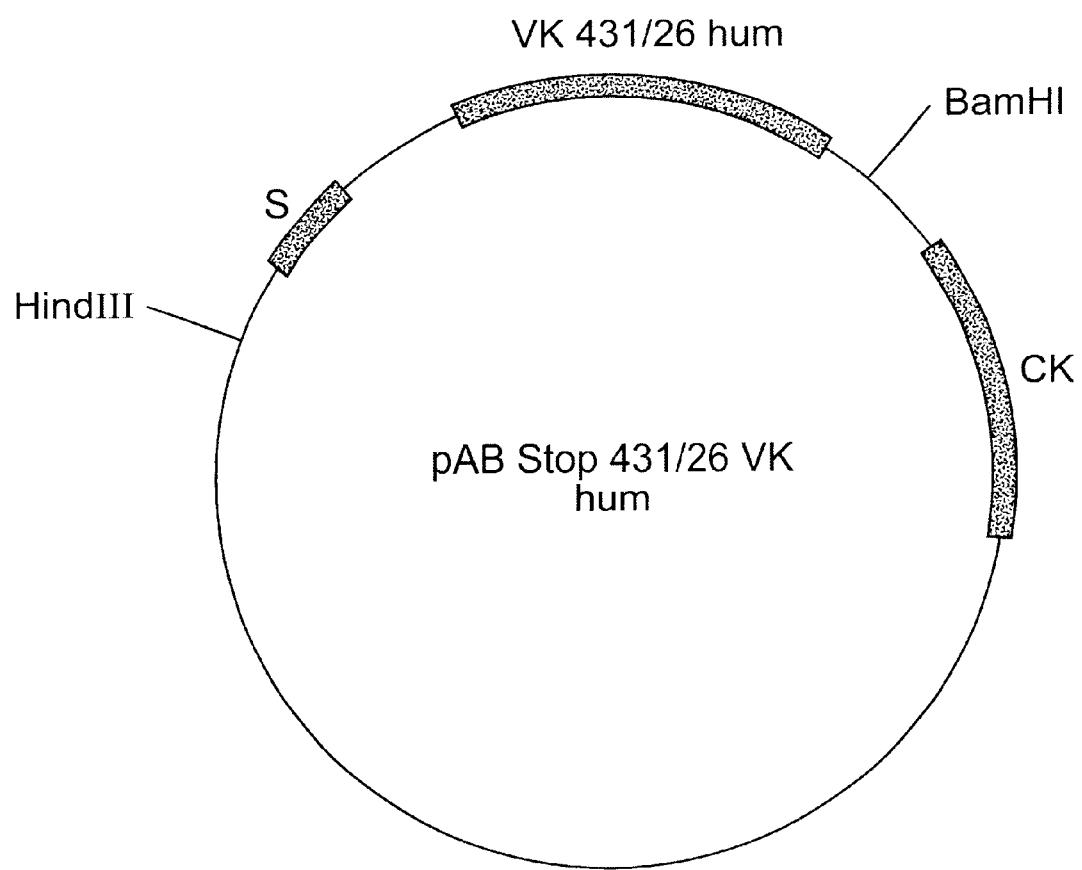
FIG. 9: Restriction map of plasmid pABStop 431/26 V$_k$ hum.

The expression vector pABstop (FIG. 9) was cleaved with HindIII and SalI. The plasmid pUC CH$_1$+H+huβGlc was cleaved with HindIII and partially with SalI and the CH$_1$+H+huβGlc insert was isolated. The CH$_1$+H+huβGlc insert was ligated to the HindIII/SalI-cleaved pABStop, and the clone pABStop CH$_1$+H+huβGlc was isolated (FIG. 7).

EXAMPLE 15

Figure 8:
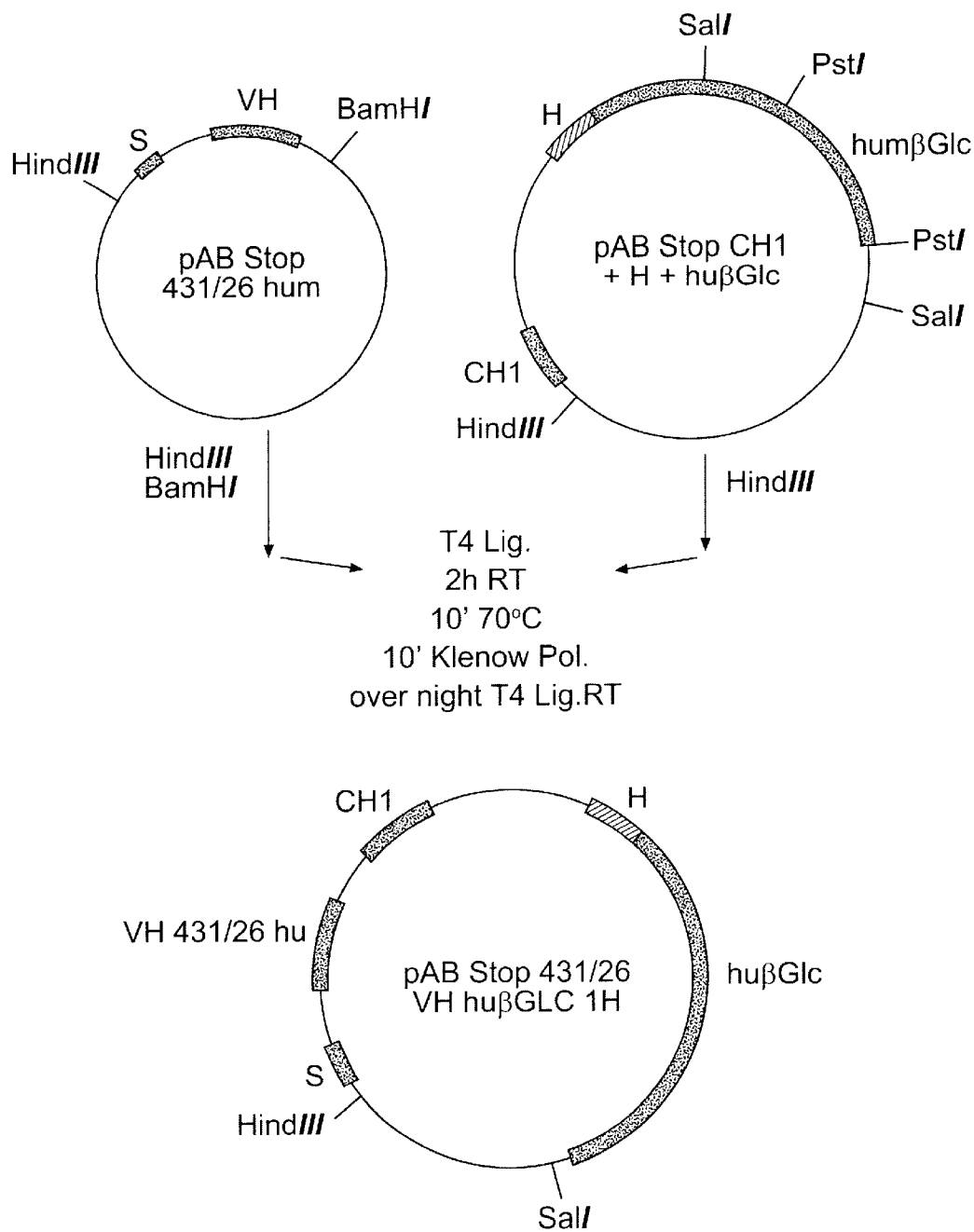
FIG. 8: Preparation of the plasmid pABStop 431/26 V$_H$ huβGlc.

The pABStop BW 431/26 hum V$_H$, which contains the humanized version of the V$_H$ gene of the anti-CEA MAb BW 431/26 (Bosslet K. et al., Eur J. Nucl. Med. 14, (1988) 523–528) (see Table 3 for the sequences of the humanized V$_H$ (SEQ. ID NOS: 5–6) and V$_K$ (SEQ. ID NOS: 7–8) genes), was cleaved with HindIII and BamHI, and the insert which contains the signal exon and the V$_H$ exon was isolated. The plasmid clone pABStop CH$_1$+H+huβGlc was cleaved with HindIII and ligated to the HindIII/BamHI 431/26 hum V$_H$ fragment. After ligation at room temperature for 2 h, the ligation was stopped by incubation at 70° C. for 10 minutes, and the ends which were still free were filled with Klenow polymerase and dNTPs. Further ligation was thencarried out overnight. After transformation, the clone pABStop 431/26 hum V$_H$ huβGlc1H which contains an immunoglobin F(ab')$_2$ gene with a hinge exon, which is fussed to the coding region of human β-glucuronidase, was isolated with the aid of restriction mapping and nucleic acid sequence analysis (FIG. 8).

EXAMPLE 16

Figure 10:
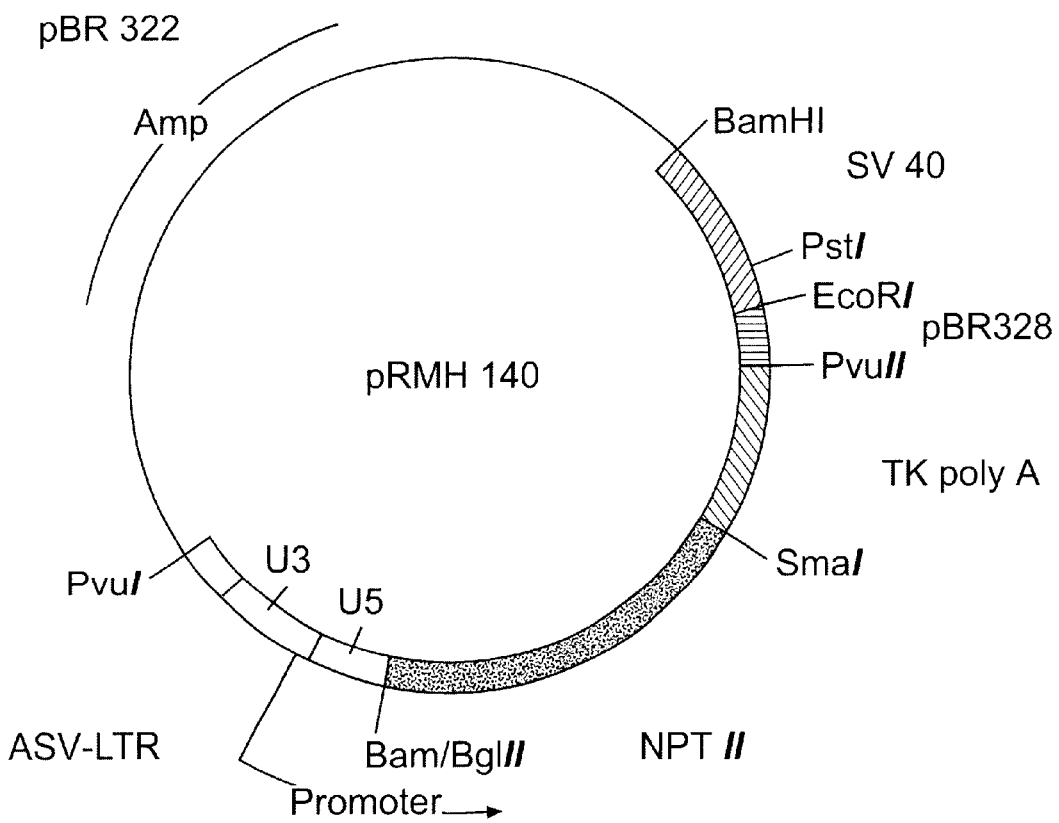
FIG. 10: Restriction map of plasmid pRMH140.
Figure 11:
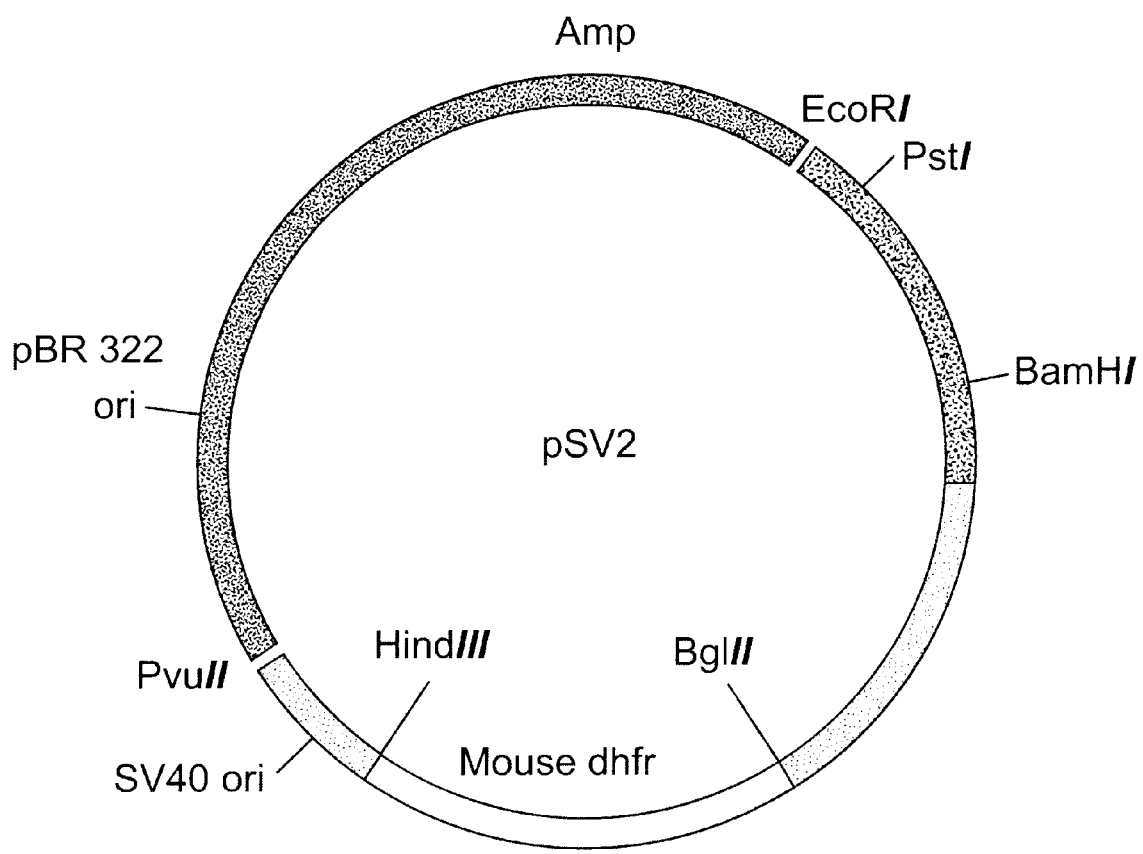
FIG. 11: Restriction map of plasmid pSV2.

The clonepABStop 431/26 V$_H$ huβGlc1H was transferred together with a plasmid clone which carries the light chain of humanized BW 431/26 (FIG. 9) and two plasmids which carry a neomycin- (FIG 10) and a methotrexate-resistance gene (FIG.11) into BHK cells. A fusion protein which has both the antigen-binding properties of Mab BW 431/26hum and the enzymatic activity of human β-glucuronidase was expressed.

EXAMPLE 17

Demonstration of the Antigen-binding Properties and of the Enzymatic Activity of the 431/26 hum V$_H$huβlc 1H Fusion Protein.

The ability of the 431/26 hum V$_H$huβGlc 1H fusion protein to bind specifically to the epitope defined by 431/26 on CEA (carcinoembryonic antigen) and, at the same time, to exert the enzymatic activity of human β-glucuronidase was determined in a specificity/enzyme activity assay. This assay is carried out as described below:

Polystyrene (96-well) microtiter plates (U shape, Type B, supplied by Nunc, Order No. 4-60445) are incubated with purified CEA (1–5 μg of CEA/ml, 75 μl of this per well) or with GIT mucin (same amount as CEA) at room temperature overnight.

The non-adsorbed antigen is removed by aspiration and washed 3× with 0.05 M tris/citrate buffer, pH 7.4.

The microtiter plates are left to stand at room temperature with the opening facing downwards on cellulose overnight.

The microtiter plates are incubated with 250 μl of 1% strength casein solution in PBS, pH 7.2, per well (blocking solution) at 20° C. for 30 minutes.

TABLE 3

```
431/26 VH hum
        10                  30                  50
caactgcaggagagcggtccaggtcttgtgagacctagccagaccctgagcctgacctgc
GlnLeuGlnGluSerGlyProGlyLeuValArgProSerGlnThrLeuSerLeuThrCys
        70                  90                  110
accgtgtctggcttcaccatcagcagtggttatagctggcactgggtgagacagccacct
ThrValSerGlyPheThrIleSerSerGlyTyrSerTrpHisTrpValArgGlnProPro
        130                 150                 170
ggacgaggtcttgagtggattggatacatacagtacagtggtatcactaactacaaccc
GlyArgGlyLeuGluTrpIleGlyTyrIleGlnTyrSerGlyIleThrAsnTyrAsnPro
        190                 210                 230
tctctcaaaagtagagtgacaatgctggtagacaccagcaagaaccagttcagcctgaga
SerLeuLysSerArgValThrMetLeuValAspThrSerLysAsnGlnPheSerLeuArg
        250                 270                 290
ctcagcagcgtgacagccgccgacaccgcggtctattattgtgcaagagaagactatgat
LeuSerSerValThrAlaAlaAspThrAlaValTyrTyrCysAlaArgGluAspTyrAsp
        310                 330                 350
taccactggtacttcgatgtctggggtcaaggcagcctcgtcacagtctcctca (SEQ. ID No: 5)
TyrHisTrpTyrPheAspValTrpGlyGlnGlySerLeuValThrValSerSer (SEQ. ID No: 6)
431/26 VK hum
        10                  30                  50
ggtgtccactccgacatccagatgacccagagcccaagcagcctgagcgccagcgtgggt
GlyValHisSerAspIleGlnMetThrGlnSerProSerSerLeuSerAlaSerValGly
        70                  90                  110
gacagagtgaccatcacctgtagtaccagctcgagtgtaagttacatgcactggtaccag
AspArgValThrIleThrCysSerThrSerSerSerValSerTyrMetHisTrpTyrGln
        130                 150                 170
cagaagccaggtaaggctccaaagctgctgatctacagcacatccaacctggcttctggt
GlnLysProGlyLysAlaProLysLeuLeuIleTyrSerThrSerAsnLeuAlaSerGly
        190                 210                 230
gtgccaagcagattcagcggtagcggtagcggtaccgacttcaccttcaccatcagcagc
ValProSerArgPheSerGlySerGlySerGlyThrAspPheThrPheThrIleSerSer
        250                 270                 290
ctccagccagaggacatcgccacctactactgccatcagtggagtagttatccacgttc
LeuGlnProGluAspIleAlaThrTyrTyrCysHisGlnTrpSerSerTyrProThrPhe
        310                 330
ggccaagggaccaaggtggaaatcaaacgt (SEQ. ID No:7)
GlyGlnGlyThrLysValGluIleLysArg (SEQ. ID No:8)
```

During the blocking, the substrate is made up. The amount of substrate depends on the number of supernatants to be assayed. The substrate is made up fresh for each assay.

Substrate: 4-methylumbelliferyl β-D-glucuronide (Order No.: M-9130 from Sigma), 2.5 mM in 200 mM sodium acetate buffer, pH 5.0, with 0.01% BSA.

The blocking solution is removed by aspiration, and in each case 50 µl of BHK cell supernatant which contains the fusion protein are loaded onto the microtiter plate coated with CEA or GIT mucin (that is to say the sample volume required is at least 120 µl).

Incubation at room temperature is then carried out for 30 minutes.

The plates are washed 3× with ELISA washing buffer (Behring, OSEW 96).

The substrate is loaded in (50 µl/well) and incubated at 37° C. for 2 hours. The plate is covered because of the possibility of evaporation.

After 2 hours, 150 µl of stop solution are pipetted into each well (stop solution=0.2 M glycine +0.2% SDS, pH 11.7).

Evaluation can now be carried out under a UV lamp (excitation energy 380 nm) or in a fluorescence measuring instrument (Fluoroscan II, ICN Biomedicals, Cat. No.: 78-611-00).

It was possible to show using this specificity/enzyme activity assay that fluorescent 4-methylumbelliferol was detectable in the wells coated with CEA when the enzyme activity was determined at pH 5, the catalytic optimum (Table 4).

TABLE 4

Dilution out of fusion protein cell culture supernatant (B73/2) on CEA and GIT mucin.

| Dilution steps | 0.2M sodium acetate buffer + 0.01% BSA, pH 5, on CEA | Substrate in various solutions | |
|---|---|---|---|
| | | PBS, pH 7.2, on CEA | PBS, pH 7.2 on GIT mucin |
| Concentrated | 9118 | 2725 | 115.7 |
| 1:2 | 7678 | 2141 | 93.37 |
| 1:4 | 4662 | 1195 | 73.39 |
| 1:8 | 2927 | 618.5 | 60.68 |
| 1:16 | 1657 | 332.1 | 53.69 |
| 1:32 | 853 | 168.2 | 40.44 |
| 1:64 | 425 | 99.26 | 48.21 |
| 1:128 | 192.5 | 57.89 | 47.48 |

Determination of the conversion rate at pH 7.2 showed that at this physiological pH that of the fusion protein was still=25% of the conversion rate at pH 5. No significant methylumbelliferol liberation was measurable on the negative control plates coated with GIT mucin and measured at pH 5. This finding shows that the humanized V region of the 431/26hum $V_H$huβGlc 1H fusion protein has retained its epitope specificity, and the β-glucuronidase portion of the fusion protein is able, like the native human enzyme, to cleave the β-glucuronide of 4-methylumbelliferol.

EXAMPLE 18

Demonstration of the Functional Identity of the V Region of the 431/26hum $V_H$huβGlc 1H Fusion Protein With That of the Humanized MAb BW 431/26 and That of the Murine MAb BW 431/26.

It was shown in Example 17 that the 431/26hum $V_H$huβGlc 1H fusion protein has a certain CEA-binding potential and β-glucuronidase activity. The antigen-specific competitive assay described hereinafter provides information on the identity of the CEA epitopes which are recognized by the competing molecules, and on the strength of the epitope/fusion protein and epitope/antibody interactions.

This assay is carried out as described below:

Polystyrene 96-well microtiter plates (U shape, Type B, supplied by Nunc, Order No. 4-60445) are incubated with purified CEA (1–5 µg of CEA/ml, 75 µl of this per well) or with. GIT mucin (same amount as CEA) at room temperature overnight.

The non-adsorbed antigen is removed by aspiration and washed 3× with 0.05 M tris/citrate buffer, pH 7.4.

The microtiter plates are left to stand at room temperature with the opening facing downwards on cellulose overnight.

The microtiter plates are incubated with 250 µl of 1% strength casein solution in PBS, pH 7.2, per well (blocking solution) at room temperature for 30 minutes.

50 µl of the MAb BW 431/26 in a concentration of 5 ng/ml are mixed with 50 µl of 10-fold concentrated supernatant of the humanized MAb BW 431/26 or of the fusion protein, as well as serial 2×dilutions.

50 µl aliquots of these mixtures are pipetted into the wells of microtiter plates coated with CEA or GIT mucin.

The microtiter plates are incubated at room temperature for 30 minutes.

The plates are then washed 3× with ELISA washing buffer (supplied by Behringwerke AG, Order No. OSEW 96, 250 µl).

Then 50 µl of a 1:250-diluted goat anti-mouse Ig antibody which is coupled to alkaline phosphatase (Southern Biotechnology Associates, Order No.: 1010-04) are added.

After incubation at R.T. for 30 minutes and washing 3 times, the substrate reaction is carried out as follows:

Add 30 µl of 0.1 mM NADP per well (dissolve 7.65 mg in 100 ml of 20 mM tris; 0.1 mM MgSO$_4$, pH 9.5); the solution can be stored at −20° C. for several months.

Incubate at room temperature for 30 minutes.

Make up the enhancer system during the incubation with NADP:

(5 ml per plate)

2 parts of INT (dissolve 2.5 mg/ml in 30% strength ethanol in an ultrasonic bath; always make up fresh) +1 part of PBS, pH 7.2 +1 part of diaphorase (1 mg/ml PBS, pH 7.2) +1 part of ADH (0.5 mg/ml PBS, pH 7.2)

add 50 µl of the enhancer system when the extent of reaction is as required, stop the reaction with 0.1 N H$_2$SO$_4$, 100 µl per well measure at 492 nm in a TITERTEK® MULTISCAN (blank=50 µl of NADP+50 µl, of enhancer solution+ 100 µl of 0.1 N H$_2$SO$_4$)

NADP—supplied by Sigma, Order No. N-0505

INT—supplied by Sigma, Order No. I-8377

ADH—supplied by Sigma, Order no. A-3263

Diaphorase—supplied by Sigma, Order No. D-2381

Reduction of the extinction in this antigen-specific competitive assay means that there is competition between the molecules competing with one another for epitopes which are the same or lying very close together spatially.

The inhibition data which are obtained show that both the fusion protein 431/26hum $V_H$huβGlc 1H and the humanized MAb 431/26 block binding of the murine MAb BW 431/26 to its CEA epitope. 50% inhibition is reached at a 200 molar excess of the relevant competitors. The conclusion from this is that the avidity of the fusion protein for the CEA epitope is comparable with that of the humanized MAb 431/26. Furthermore, the fusion protein and the humanized MAb bind to the same epitope or to an epitope which lies spatially very near to that defined by the murine MAb BW 431/26 on CEA.

EXAMPLE 19

Demonstration of the Tissue Specificity of the 431/26hum $V_H$huβGlc 1H Fusion Protein.

Example 17 showed, inter alia, that the 431/26hum $V_H$huβGlc 1H fusion protein is able to bind to purified CEA.

Example 18 showed that the V region of the fusion protein is able to compete with the V region of murine BW 431/26 for the same, or a very close, epitope. The indirect immunohistochemical assay which is specific for β-glucuronidase and is described hereinafter can be used to determine the microspecificity of the fusion protein on cyropreserved tissues.

The assay is described below:

6 μm-thick frozen sections are placed on slides and dried in air for at least 30 minutes.

The slides are subsequently fixed in acetone at −20° C. for 10 seconds.

The slides are washed in tris/NaCl washing buffer, pH 7.4, with 0.1% BSA for 5 minutes.

20–100 μl of fusion protein-containing BHK cell supernatant (concentrated or diluted in tris/BSA, pH 7.4) is applied to each section and incubated in a humidity chamber at room temperature for 30 minutes.

The slides are washed in tris/NaCl washing buffer, pH 7.4, with 0.1% BSA for 5 minutes.

50 μl of hybridoma supernatant of the murine anti-β-glucuronidase MAb BW 2118/157 are added to each section, and the slides are incubated in a humidity chamber at room temperature for 30 minutes.

The slides are then washed in tris/NaCl washing buffer, pH 7.4, with 0.1% BSA for 5 minutes.

20–100 μl of bridge Ab (rabbit-antimouse IgG diluted 1:100 in human serum, pH 7.4) are applied to each section and incubated in a humidity chamber at room temperature for 30 minutes.

The slides are then washed in tris/NaCl washing buffer, pH 7.4, with 0.1% BSA for 5 minutes.

Subsequently 20–100 μl of APAAP complex (mouse anti-AP diluted 1:100 in tris/BSA, pH 7.4) are applied to each section and incubated in a humidity chamber at room temperature for 30 minutes.

The slides are then washed in tris-NaCl washing buffer, pH 7.4, with 0.1% BSA for 5 minutes.

The substrate for alkaline phosphatase is made up as follows (100 ml of substrate solution sufficient for one glass cuvette):

Solution 1: 3.7 g of NaCl 2.7 g of tris base (dissolve in 75 ml of distilled water) +26.8 ml of propanediol buffer, pH 9.75, adjust with HCl +42.9 mg of levamisole→clear, color-less solution Solution 2: Dissolve 21.4 mg of sodium nitrite in 535 μl of distilled water →clear, colorless solution Solution 3: Dissolve 53.5 mg of naphthol AS BI phosphate in 642 μl of dimethylformamide (DMF) →clear, yellowish solution Add 368 μl of 5k strength new fuchsin solution to solution 2 (sodium nitrite) and leave to react for 1 minute (stopclock) to give a clear, brown solution.

Add solution 2 (sodium nitrite with new fuchsin) and solution 3 (naphthol AS BI phosphate) to solution 1 (tris/NaCl/propanediol buffer)→clear, yellowish solution.

adjust to pH 8.8 with HCl=cloudy, yellowish solution filter solution and place on the slide and leave to react on a shaker for 15 minutes→solution becomes cloudy.

wash slide in tris/NaCl buffer, pH 7.4, for 10 minutes.

wash slide in distilled water for 10 minutes after drying in air for 2 hours, the slides are sealed in Kaiser's glycerol/gelatin at 56° C.

Specific binding of the fusion protein was demonstrated under the light microscope by the red coloration of the epitope-positive tissue sections. Comparative investigations with the murine MAb BW 431/26, which was detected by the indirect APAAP technique (Cordell et al. (1984) J. Histochem. Cytochem. 32, 219), revealed that the tissue specificity of the fusion protein agreed exactly with that of the murine MAb BW 431/26, i.e. that there is identity both of the reaction type in the individual specimen and of the number of positive and negative findings from a large number of different carcinomas and normal tissue.

EXAMPLE 20

Purification of the 431/26hum $V_H$huβGlc 1H Fusion Protein.

Murine and humanized MAbs can be purified by immunoaffinity chromatography methods which are selective for the Fc part of these molecules. Since there is no Fc part in the 431/26 hum $V_H$huβGlc 1H fusion protein, it was necessary to develop an alternative highly selective immunoaffinity chromatography method. Besides the selectivity of this method to be developed, it is necessary for the isolation conditions to be very mild in order not to damage the β-glucuronidase, which is very labile in the acidic and in the alkaline range.

The principle of the method comprises purification of the fusion protein from supernatants from transfected BHK cells using an anti-idiotype MAb directed against the humanized V region. The preparation of such MAbs is known from the literature (Walter et al. (1988) Behring Inst. Mitt. 82, 182–192). This anti-idiotype MAb can be both murine and humanized. The MAb is preferably immobilized on a solid phase so that its V region has not been damaged. Examples of this are known from the literature (Fleminger et al. (1990) Applied Biochem. Biotechnol. 23, 123–137; Horsfall et al. (1987) JIM 104 43–49).

The anti-idiotype MAb thus immobilized on the solid phase by known methods binds very efficiently the fusion protein to be purified from transfected BHK cells, for example at pH 7, but has the surprising property that it no longer binds the fusion protein when the pH is lowered by only 1.5, to pH 5.5. This mild pH elution technique has no adverse effect on the fusion protein, either in its ability to bind to CEA or in its enzymatic activity (for methods, see Example 17). Table 5 shows the OD values and fluorogenic units (FU) of the individual fractions from a purification using the solid phase-immobilized, anti-idiotype MAb BW 2064/34.

TABLE 5

| Anti-idiotype affinity chromatography. | | | | |
|---|---|---|---|---|
| Fractions | OD in % | FU in % | pH | Chromatography procedure |
| 1–5 | 1 | 0 | 7.2 | Preliminary washing of the column with PBS, pH 7.2 |

TABLE 5-continued

Anti-idiotype affinity chromatography.

| Fractions | OD in % | FU in % | pH | Chromatography procedure |
|---|---|---|---|---|
| 6–142 | 20 | 0 | 7.2 | Sample loading |
| 143–162 | 1 | 0 | 7.2 | Washing of the column with PBS, pH 7.2 |
| 163 | 1 | 0 | 7.2 | |
| 164 | 1 | 0 | 7.2 | |
| 165 | 1 | 0 | 7.2 | |
| 166 | 1 | 0 | 6.8 | |
| 167 | 2 | 10 | 6.1 | |
| 168 | 5 | 20 | 5.7 | |
| 169 | 16 | 40 | 5.6 | |
| 170 | 23 | 80 | 5.5 | |
| 171 | 26 | 100 | 5.4 | Elution with PBS, pH 4.2 |
| 172 | 24 | 80 | 5.3 | |
| 173 | 19 | 60 | 5.2 | |
| 174 | 14 | 40 | 5.2 | |
| 175 | 10 | 30 | 5.1 | |
| 176 | 8 | 25 | 5.1 | |
| 177 | 6 | 20 | 5.1 | |
| 178 | 3 | 10 | 5.0 | |
| 179 | 2 | 5 | 5.0 | |
| 180 | 1 | 0 | 5.0 | |

1 fraction=collection for 6.6 min (at pumping rate of 18 ml/h)=2 ml

The FU values are indicated as k of the highest value (fraction 171).

The elution of the fusion protein was measured as protein by measurement of the OD at 280 nm. In addition, the isolated fractions were examined for specific binding to CEA and simultaneous enzyme activity in the specificity/enzyme activity assay (Example 17). The values show that all the specific binding and enzyme activity was concentrated in one peak (peak eluted from around pH 5.0 to pH 5.6). The conclusion from this is that the described method of anti-idiotype affinity chromatography is a very efficient and selective purification technique for the 431/26hum $V_H$huβGlc 1H fusion protein.

EXAMPLE 21

Gel Chromatography of the Fusion Proteins.

The supernatants from the BHK cells secreting the 431/26hum $V_H$huβGlc 1H fusion protein (B 70/6, B 74/2, B 72/72, B 73/2) were removed, sterilized by filtration and subjected to analytical gel filtration. For this, a TSK G3000 SW-XL column (7.8×300 mm) was equilibrated with 0.1 M sodium phosphate buffer, pH 6.7, +0.02% NaN$_3$, 20 μl of the supernatant were loaded on, and elution was carried out with a flow rate of 0.6 ml/min. Starting with an elution time of 9 min (exclusion volume 9.5 min), fractions (0.3 min each) were collected and assayed for β-glucuronidase activity.

For this 25 μl of the particular fraction were mixed with 75 μl of substrate solution (2.5 mM 4-methylumbelliferyl β-glucuronide in 200 mM sodium acetate buffer, pH 5, +0.1 mg/ml BSA) and incubated at 37° C. for 2 hours. The reaction was then stopped with 1.5 ml of 0.2 M glycine/0.2% SDS solution, pH 11.7, and the fluorescent label liberated by the glucuronidase was quantified in a Hitachi fluorometer (with excitation wavelength of 360 nm and emission wavelength of 450 nm).

Result:

All 4 constructs show a single main activity peak between fractions 4 and 6 (Table 6). This corresponds to retention times of about 10.2–10.8 min. The fusion proteins with glucuronidase activity in the supernatants thus have retention times which are of the same order of magnitude as those of chemically prepared antibody-β-glucuronidase constructs (10.4 min). The retention time for the free enzyme is 11.9, and for the free antibody is 12.3 min.

TABLE 6

Gel filtration of various fusion proteins.
Incubation: 25 μl, 37° C., 120 min
Substance concentration: 1.875 mM; 0.1 mg/ml BSA
Each fraction 0.3 min; start at 9 min

| | Liberated label/assay (FU) | | | |
|---|---|---|---|---|
| Fractions | B70/6 | B74/2 | B72/72 | B73/2 |
| 1 | 11 | 17 | 15 | 15 |
| 2 | 22 | 35 | 44 | 38 |
| 3 | 125 | 97 | 873 | 1014 |
| 4 | 1072 | 196 | 2959 | 3994 |
| 5 | 1588 | 165 | 2206 | 3141 |
| 6 | 1532 | 120 | 1133 | 1760 |
| 7 | 941 | 103 | 581 | 926 |
| 8 | 710 | 69 | 376 | 723 |
| 9 | 500 | 108 | 302 | 626 |
| 10 | 371 | 123 | 316 | 613 |
| 11 | 320 | 107 | 263 | 472 |
| 12 | 254 | 91 | 210 | 456 |
| 13 | 224 | 57 | 146 | 357 |
| 14 | 190 | 65 | 134 | 332 |
| 15 | 171 | 52 | 83 | 294 |
| 16 | 167 | 44 | 99 | 243 |
| 17 | 100 | 38 | 73 | 217 |
| 18 | 129 | 34 | 55 | 179 |
| 19 | 75 | 45 | 48 | 155 |
| 20 | 66 | 41 | 36 | 129 |
| 21 | | | | 118 |
| 22 | | | | 93 |
| 23 | | | | 78 |
| 24 | | | | 61 |
| 25 | | | | 24 |
| 26 | | | | 51 |

EXAMPLE 22

Molecular Characterization of the 431/26 hum $V_H$huβGlc1H fusion protein.

The fusion proteins were purified by anti-idiotype affinity chromatography in Example 20. Aliquots from the peak eluted at pH 5.5 were subjected to 10% SDS PAGE electrophoresis under non-reducing and reducing conditions and immunostained in a Western blot using anti-idiotype MAbs or with anti-β-glucuronidase MAbs (Towbin and Gordon (1979) Proc. Natl. Acad. Sci. USA 76, 4350–4354).

Figure 12A:
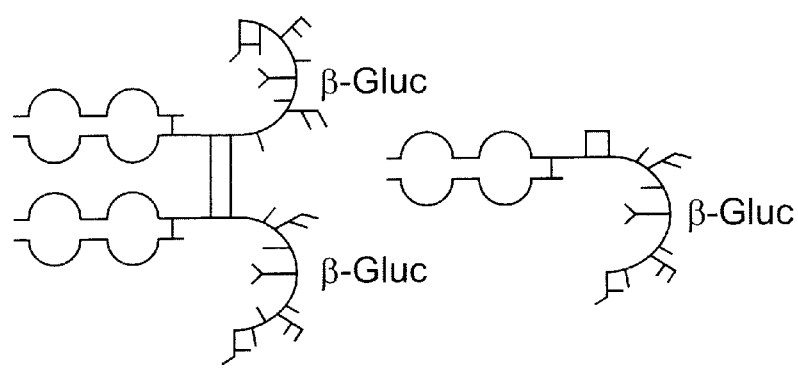
FIG. 12: Diagrammatic representations of the 431/26 hum V$_H$ huβGlc1H fusion protein: (A) a monomer and dimer linked by interchain disulfide bridges can be detected under denaturing conditions; (B) a monomer; (C) dimers, with or without interchain disulfide bridges, can be detected under native conditions.
Figure 12B:
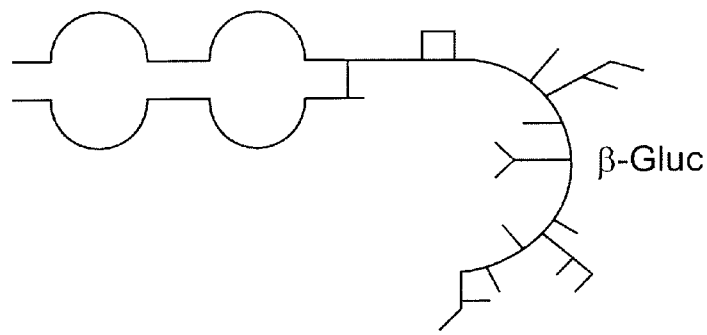
Figure 12C:
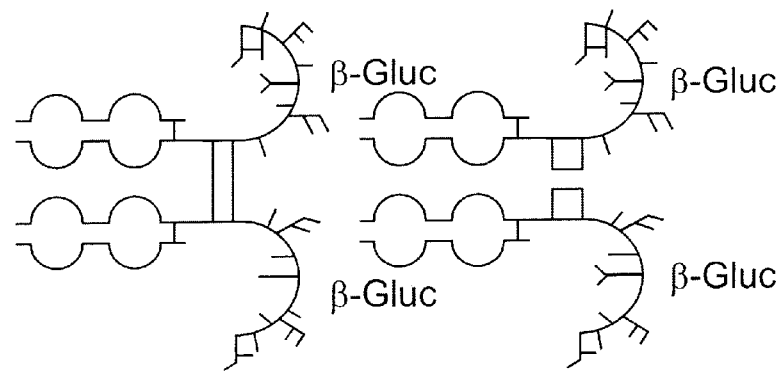

Under non-reducing conditions with the 431/26 hum $V_H$huβGlc1H fusion protein, a main band of ≈125 kDa and a band of 250 kDa were detected and were detectable both by anti-idiotype MAb and by anti-β-glucuronidase MAb in the Western blot. Under reducing conditions there was no detectable immunostaining either by the anti-idiotype or by the anti-β-glucuronidase MAbs. A 100 kDa and a 25 kDa band were detected in the reducing SDS PAGE. However, these molecules analyzed under denaturing conditions are, according to TSK G 3000 SW-XL gel filtration under native conditions, in the form of a higher molecular weight product which has a molecular weight of ≈250 kDa (Example 2). Diagrammatic representations of the 431/26 hum $V_H$huβGlc 1H fusion protein are shown in FIG. 12. FIG. 12 B shows the monomer which has a ≈25 kDa light chain and a ≈100 kDa heavy chain. This monomer and dimer linked by inter-heavy chain disulfide bridges can be detected under denaturing conditions (FIG. 12A). Under native conditions, the fusion protein is in the form of a dimer of ≈250 kDa, with or withiut inter-heavy chain disulfide bridges (FIG. 12C).

EXAMPLE 23

Chemical Modification of the Fusion Protein.

The fusion protein purified as in Example 21 (110 μg/ml) was adjusted to pH 4.5 and mixed with sodium periodate (final concentration 1 mM). After incubation at room temperature in the dark for 1 hour, the sodium periodate was removed by gel chromatography, and the fusion protein was then readjusted to pH 8. Addition of ethanolamine to a final concentration of 0.1 M was followed by incubation at 4° C. for a further 3 hours, then sodium cyanoborohydride (final concentration 5 mM) was added and incubated for 30 min (reduction). This was followed by another gel filtration to remove the reducing agent and to change the buffer of the fusion protein. The chemical modification had no effect on the functional activity of the fusion protein. Table 7 shows the change in the plasma concentrations of unmodified and modified fusion protein in the nude mouse. The elimination of the fusion protein from the plasma is greatly slowed down by the modification.

TABLE 7

Plasma levels of β-glucuronidase activity in the nude mouse.

| | β-Glucuronidase fusion protein | |
|---|---|---|
| t [min] | Treated % activity | Untreated % activity |
| 0 | 100 | 100 |
| 10 | | 54 |
| 30 | 76 | |
| 60 | | 22 |
| 240 | 40 | 4 |
| 480 | | 1 |
| 1380 | 19 | |
| 1440 | | 1 |
| 5880 | 3 | |

EXAMPLE 24

Enzymatic Treatment of the Fusion Protein.

53 μg of fusion protein (Example 21) in 0.01 M tris/HCl, 0.15 M NaCl were incubated with 1 unit of soluble alkaline phosphatase (*E. coli*) or immobilized alkaline phosphatase (bovine intestine) at room temperature for 20 h. Table 8 shows the change in the plasma concentration of untreated and treated fusion protein in the nude mouse. The elimination is not significantly affected by the enzyme treatment.

TABLE 8

Plasma levels of β-glucuronidase activity in the nude mouse.

| | β-Glucuronidase fusion protein | | |
|---|---|---|---|
| t [min] | untreated [%] | AP (bovine intestine, immobil.) treated [%] | AP (*E. coli*) treated [%] |
| 0 | 100 | 100 | 100 |
| 10 | 78 | 76 | 65 |
| 30 | 44 | 57 | 53 |
| 60 | 35 | 36 | 35 |
| 240 | 22 | 27 | 22 |
| 1440 | 4 | 5 | 5 |

AP = alkaline phosphatase

EXAMPLE 25

Pharmacokinetics and Tumor Retention of the 431/26 hum $V_H$ huβGlc 1H Fusion Protein.

By way of example, 5×4 μg of purified fusion protein which was mixed with 100 μg of HSA/ml were injected in unmodified (Example 21) and chemically modified form (Example 23) i.v. at 24-hour intervals into CEA-expressing nude mice harboring human tumors. After defined time intervals, 3 animals in each case were sacrificed by cervical dislocation. The organs were removed, weighed and mixed with 2 ml of 1% strength BSA in PBS, pH 7.2. The tissue and cells from these organs were then broken down in a Potter (10 strokes) and the amount of functionally active fusion protein was determined in the supernatant after centrifugation of the suspension at 3000 rpm and room temperature for 10 minutes (Heraeus Labofuge GL, Type 2202) in the specificity/enzyme activity assay (see Example 17). The date from a representative experiment are shown in Table 9. It is clearly evident that the chemically modified fusion protein, which has a t1/2β of ≅4 h, specifically accumulates in the tumor from ≧3 days after completion of the repetitive injection phase. The unmodified fusion protein, which has a t1/2β of ≅20 min, showed no significant accumulation in the tumor under the same experimental conditions.

It may be concluded from these data that the hu 431 β-Gluc fusion protein is able to bind in vivo to CEA-positive tumors and to remain there as enzymatically active molecule over long time periods (>9 days). The time the prodrug is administered in this system should be between day 3 and 9 after completion of the fusion protein injection.

TABLE 9

Tumor retention experiment with CEA-positive human stomach carcinoma xenograft (Mz Stol)
i.v. Injection of 5 × 4 μg of fusion protein per mouse at intervals of 24 hours

| Time (h) after last i.v. injection | 0% Activity/g of tumor or organ | | | | | | |
|---|---|---|---|---|---|---|---|
| | Tumor | Liver | Lung | Spleen | Kidney | Intestine | Plasma |
| 3 | 100 | 100 | 100 | 100 | 100 | 100 | 100 |
| 24 | 86.7 | 49.3 | 26.3 | — | 64 | 123 | 44.4 |
| 72 | 26.4 | 11 | 4.4 | — | 8.1 | 19 | 6.5 |
| 216 | 24.4 | 1.5 | 0.13 | 1.2 | 0.4 | 0.5 | 0.015 |

EXAMPLE 26
Isoelectric Focusing of the 431/26 hum $V_H$ huβGlc 1H fusion protein.

The fusion protein purified by anti-idiotype affinity chromatography (Example 21) was subjected to isoelectric focusing in the Pharmacia Fast System by the method of Righetti et al. (1979). It emerged from this that the isoelectric point of the molecule lies in a pH range from 7.35 to 8.15.

EXAMPLE 27
Demonstration That a Cytostatic Prodrug can be Cleaved by the 431/26 hum $V_H$ huβGlc 1H Fusion Protein.

It was shown in Example 17 that the β-glucuronidase portion of the fusion protein is able, like the native human enzyme, to cleave the β-glucuronide of 4-methylumbelliferol. In the investigations which are described hereinafter, the substrate used for the enzymatic cleavage was a β-glucuronide, linked via a spacer group, of the cytostatic daunomycin. The specific procedure for these investigations was as follows:

4 mg of the compound N-(4-hydroxy-3-nitrobenzyloxycarbonyl)daunorubicin β-D-glucuronide (prodrug), which is described in French Patent Application (No. d'Enregistrement National: 9105326) were dissolved in 1 ml of 20 mM phosphate buffer, pH 7.2. 35 μl of the fusion protein (Example 21) or of human β-glucuronidase (total concentration in each case 6.5 U/ml; 1 U=cleavage of 1 μmol of 4-methyl-umbelliferol/min at 37° C.) were pipetted into 5 μl portions of this substrate solution and incubated in the dark at 37° C. Samples (5 μl) of the incubation mixture were removed after various times and immediately analyzed by high pressure liquid chromatography under the following conditions:

Column:

Nucleosil 100 RP 18, 5 μm particle diameter, 125×4.6 mm

Mobile phase:

Gradient of solution A (100% acetonitrile) and solution B (20 mM phosphate buffer pH.3.0)

0 min: 30% solution A 15 min: 70% solution A 20 min: 70% solution A

Flow rate: 1 ml/min

Detection: fluorescence, excitation 495 nm, emission 5160 nm

Data analysis: Beckman System Gold Software

The retention time of the starting compound (prodrug) under these chromatography conditions was 11 min. The compound produced during the incubation (drug) had a retention time of 8.9 min, identical to daunomycin (DNM, analysis of a standard under the same conditions). The kinetics of the cleavage of the starting compound by the fusion protein and human β-glucuronidase are shown in Table 11 and Table 10 respectively.

The half-life of the cleavage of the prodrug by the fusion protein was 2.3 h. Cleavage by human β-glucuronidase took place with a half-life of 0.8 h. As already demonstrated in Example 17, the results of the investigations show that the β-glucuronidase portion of the fusion protein is functionally active and able to cleave β-glucuronides. The kinetics of the elimination of the glucuronide portion and the liberation of the drug (daunomycin) from the prodrug used show a rate comparable in magnitude to human β-glucuronidase, so that the substrate specificity of the fusion protein essentially agrees with that of human β-glucuronidase.

TABLE 10

Kinetics of prodrug cleavage by β-glucuronidase (human, recombinant)

| t min | Prodrug area % | DNM area % |
|---|---|---|
| 0 | 99.2 | 0.8 |
| 57 | 36.0 | 64.0 |
| 130 | 10.3 | 89.7 |
| 227 | 9.3 | 90.7 |

TABLE 11

Kinetics of prodrug cleavage by β-glucuronidase (fusion protein)

| t min | Prodrug area % | DNM area % |
|---|---|---|
| 0 | 98.9 | 1.1 |
| 50 | 81.1 | 18.9 |
| 135 | 51.7 | 48.3 |
| 190 | 33.0 | 67.0 |
| 247 | 22.0 | 78.0 |
| 317 | 12.4 | 87.6 |

What is claimed is:

1. A 4'-O-glycosyl-etoposide of the formula I:

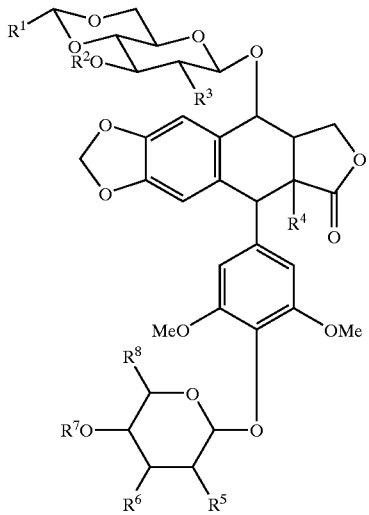

in which

R$^1$ is a methyl, benzyl or thienyl group;

R$^2$ is a hydrogen atom, an acyl or tri-C$_1$–C$_4$-alkylsilyl protective group;

R$^3$ is a hydroxyl group, an acyl or tri-C$_1$–C$_4$-alkylsilyl protective group which is bonded via an oxygen atom, an amino, acetylamino, benzyloxycarbonylamino or dimethylamino group;

R$^4$ is a hydrogen atom or a methyl group;

R$^5$ is a hydrogen atom, a hydroxyl group, an acyl or tri-C$_1$–C$_4$-alkylsilyl protective group which is bonded via an oxygen atom, or an amino, benzyloxycarbonylamino, azido or acetylamino group;

R$^6$ is a hydroxyl group, an acyl or tri-C$_1$–C$_4$-alkylsilyl protective group which is bonded via an oxygen atom, or an amino, benzyloxycarbonylamino or azido group;

R$^7$ is a hydrogen atom, an acyl or tri-C$_1$–C$_4$-alkylsilyl protective group; and R$^8$ is a methyl or hydroxymethyl group or an acyl protective group which is bonded to the ring via an oxygen of an oxymethylene group, or a benzyloxycarbonyl group;

where the acyl protective group is an acetyl, mono-, di- or trihalogenacetyl group.

2. A compound as claimed in claim 1, in which

R$^1$ is a methyl, benzyl or 2-thienyl group,

R$^2$ is a hydrogen, an acetyl or chloroacetyl group or a tri-C$_1$–C$_4$-alkylsilyl protective group, R$^3$ is a hydroxyl, acetyl, chloroacetyl or tri-C$_1$–C$_4$-alkylsilyl protective group which is bonded via an oxygen atom, or an amino, acetyl-amino, benzyloxycarbonylamino or dimethylamino group, R$^4$ is a hydrogen atom or a methyl group, R$^5$ is a hydrogen atom, ahydroxyl group, or an acetyl, chloroacetyl or tri-C$_1$–C$_4$-alkylsilyl protective group which is bonded via an oxygen atom, or an amino, benzyloxycarbonylamino, azido or acetylamino group, R$^6$ is a hydroxyl group, an acetyl, chloroacetyl or tri-C$_1$–C$_4$-alkylsilyl protective group which is bonded via an oxygen atom, or an amino, benzyloxycarbonylamino or azido group, R$^7$ is a hydrogen atom, an acetyl, chloroacetyl or tri-C$_1$–C$_4$-alkylsilyl protective group, and R$^8$ is a methyl, hydroxymethyl, acetyloxymethyl or chloroacetyloxymethyl group or a benzyloxycarbonyl group.

3. A 4'-O-glycosyl-etoposide as claimed in claim 1, wherein the acyl protective group is a trihalogenoacetyl group.

4. The 4'-O-glycosyl-etoposide as claimed in claim 3, wherein the halogen of the trihalogenoacetyl group is selected from fluorine or chlorine.

5. A pharmaceutical composition containing a compound as claimed in claim 4 and a tumor-specific enzyme of the formula II $$A\text{—}Sp\text{—}E \qquad \text{II}$$

in which

A is a humanized antibody or one of the fragments thereof, which specifically binds to a tumor-associated antigen, E is a human glycosidase; and Sp is a spacer and is an oligo- or polypeptide spacer or a bifunctional sulfide- or disulfide- containing group of the formula III or IV $$X(S)_n Y \qquad \text{III}$$

$$X(S)_n \qquad \text{IV}$$

in which

X is —CO—R$^9$—(N-succinimido)- or —C(=R$^{10}$)—CH$_2$—CH$_2$— with R$^9$ being —CH$_2$—CH$_2$—, 1,4-cyclohexylidene, 1,3- or 1,4-phenylene or methoxycarbonyl- or chloro-1,4-phenylene and R$^{10}$ being O or NH, Y is —C(=R$^{10}$)—CH$_2$—CH$_2$—, where R$^{10}$ is as defined above, and n is 1 in the case of a sulfide containing group, n is 2 in the case of a disulfide containing group.

6. A pharmaceutical composition as claimed in claim 5, wherein A—Sp—E is prepared by genetic engineering, where A and E have the meaning as in claim 5, and Sp is an oligo- or polypeptide.

7. A pharmaceutical composition as claimed in claim 5, wherein E is a glycosidase selected from the group consisting of α- or β-glucosidase, α-galactosidase, α- or β-mannosidase, α-fucosidase, N-acetyl-α- galactosaminadase, N-acetyl-β-glucosaminidase, N-acetyl-β-glucosaminidase and β-glucuronidase.

8. The pharmaceutical composition as claimed in claim 5, wherein A is a humanized antibody which has specificity for a carcinoembryonic antigen.

9. A 4'-O-glycosyl-etoposide of the formula I:

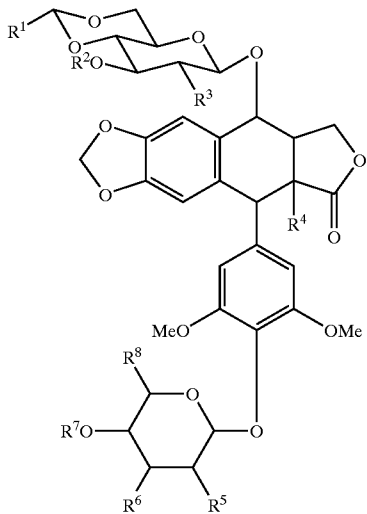

in which

R$^1$ is a methyl, benzyl or thienyl group;

R$^2$ is a hydrogen atom, an acyl or tri-C$_1$–C$_4$-alkylsilyl protective group;

R$^3$ is a hydroxyl group, an acyl or tri-C$_1$–C$_4$-alkylsilyl protective group which is bonded via an oxygen atom, an amino, acetylamino, benzyloxycarbonylamino or dimethylamino group;

R$^4$ is a hydrogen atom or a methyl group;

R$^5$ is a hydrogen atom, a hydroxyl group, an acyl or tri-C$_1$–C$_4$-alkylsilyl protective group which is bonded via an oxygen atom, or an amino, benzyloxycarbonylamino, azido or acetylamino group;

R$^6$ is a hydroxyl group, an acyl or tri-C$_1$–C$_4$-alkylsilyl protective group which is bonded via an oxygen atom, or an amino, benzyloxycarbonylamino or azido group;

R$^7$ is a hydrogen atom, an acyl or tri-C$_1$–C$_4$-alkylsilyl protective group; and R$^8$ is a methyl or hydroxymethyl group or an acyl protective group which is bonded to the ring via a methylene of an oxymethylene group, or a benzyloxycarbonyl group;

where the acyl protective group is an acetyl, mono-, di- or trihalogenacetyl group.

10. A compound as claimed in claim 9, in which

R$^1$ is a methyl, benzyl or 2-thienyl group;

R$^2$ is a hydrogen, an acetyl or chloroacetyl group or a tri-C$_1$–C$_4$-alkylsilyl protective group;

R$^3$ is a hydroxyl group, acetyl, chloroacetyl or tri-C$_1$–C$_4$-alkylsilyl protective group which is bonded via an oxygen atom, an amino, acetylamino, benzyloxycarbonylamino or dimethylamino group;

R$^4$ is a hydrogen atom or a methyl group;

R$^5$ is a hydrogen atom, a hydroxyl group, or an acetyl, chloroacetyl or tri-C$_1$–C$_4$-alkylsilyl protective group which is bonded via an oxygen atom, or an amino, benzyloxycarbonylamino, azido or acetylamino group;

R$^6$ is a hydroxyl group, an acetyl, chloroacetyl or tri-C$_1$–C$_4$-alkylsilyl protective group which is bonded via an oxygen atom, or an amino, benzyloxycarbonylamino or azido group;

R$^7$ is a hydrogen atom, an acetyl, chloroacetyl or tri-C$_1$–C$_4$-alkylsilyl protective group; and R$^8$ is a methyl or hydroxymethyl, acetyloxymethyl or chloroacetyloxymethyl group or a benzyloxycarbonyl group.

11. A pharmaceutical containing a compound as claimed in claim 9 and a tumor-specific enzyme of the formula II:

A—Sp—E   II in which

A is a humanized antibody or one of the fragments thereof, which specifically binds to a tumor-associated antigen;

E is a human or humanized glycosidase; and

Sp is a spacer and is an oligo- or polypeptide spacer or a bifunctional sulfide- or disulfide containing group of the formula III or IV X(S)$_n$Y   III X(S)$_n$   IV in which X is —CO—R$^9$—(N-succinimido) or —C(=R$^{10}$)—CH$_2$—CH$_2$— with R$^9$ being —CH$_2$—CH$_2$, 1,4-cyclohexylidene, 1,3- or 1,4-phenylene or methoxycarbonyl- or chloro-1,4-phenylene and R$^{10}$ being O or NH;

Y is —C(=R$^{10}$)—CH$_2$—CH$_2$—, where R$^{10}$ is as defined above; and n is 1 in the case of a sulfide containing group, n is 2 in the case of a disulfide containing group.

12. A pharmaceutical composition as claimed in claim 11, wherein A—S—E is prepared by genetic engineering, where A and E have the meaning as in claim 3, and Sp is an oligo- or polypeptide.

13. A pharmaceutical composition as claimed in claim 11, wherein E is a glycosidase selected from the group consisting of α- or β-glucosidase, α-galactosidase, α- or β-mannosidase, α-fucosidase, N-acetyl-α-galactosaminadase, N-acetyl-β-glucosaminadase, [N-acetyl-β-glucosaminadase] N-acetyl-α-glucosaminadase and β-glucoronidase.

14. The pharmaceutical composition as claimed in claim 11, wherein A is a humanized antibody which has specificity for a carcinoembryonic antigen.

15. A 4'-O-glycosyl-etoposide as claimed in claim 9, wherein the acyl protective group is a trihalogenoacetyl group.

16. A 4'-O-glycosyl-etoposide as claimed in claim 15, wherein the halogen of the trihalogenoacetyl group is selected from fluorine or chlorine.

* * * * *

UNITED STATES PATENT AND TRADEMARK OFFICE
CERTIFICATE OF CORRECTION

PATENT NO.   : 6,610,299 B1
DATED        : August 26, 2003
INVENTOR(S)  : Cenek Kolar et al.

It is certified that error appears in the above-identified patent and that said Letters Patent is hereby corrected as shown below:

<u>Column 34,</u>
Line 33, "claim 4" should read -- claim 1 --.

Signed and Sealed this

Eighth Day of June, 2004

JON W. DUDAS
*Acting Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GCGGCGGCGG CGGTGCA                                                    17

(2) INFORMATION FOR SEQ ID NO:2:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:2:

CCGCCGCCGC CGCTGCA                                                    17

(2) INFORMATION FOR SEQ ID NO:3:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

GAGCCCAAAT CTTGTGACAC ACCTCCCCCG TGCCCACGGT GCCCAGTTGC A               51

(2) INFORMATION FOR SEQ ID NO:4:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

ACTGGGCACC GTGGGCACGG GGGAGGTGTG TCACAAGATT TGGGCTCTGC A               51

(2) INFORMATION FOR SEQ ID NO:5:

(i) SEQUENCE CHARACTERISTICS:
            (A) LENGTH: 354 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

CAACTGCAGG AGAGCGGTCC AGGTCTTGTG AGACCTAGCC AGACCCTGAG CCTGACCTGC      60

ACCGTGTCTG GCTTCACCAT CAGCAGTGGT TATAGCTGGC ACTGGGTGAG ACAGCCACCT     120

GGACGAGGTC TTGAGTGGAT TGGATACATA CAGTACAGTG GTATCACTAA CTACAACCCC     180

TCTCTCAAAA GTAGAGTGAC AATGCTGGTA GACACCAGCA AGAACCAGTT CAGCCTGAGA     240

CTCAGCAGCG TGACAGCCGC CGACACCGCG GTCTATTATT GTGCAAGAGA AGACTATGAT     300

TACCACTGGT ACTTCGATGT CTGGGGTCAA GGCAGCCTCG TCACAGTCTC CTCA           354

(2) INFORMATION FOR SEQ ID NO:6:

(i) SEQUENCE CHARACTERISTICS:
            (A) LENGTH: 118 amino acids
            (B) TYPE: amino acid
            (D) TOPOLOGY: linear
```

(ii) MOLECULE TYPE: peptide (xi) SEQUENCE DESCRIPTION: SEQ ID NO:6:

Gln Leu Gln Glu Ser Gly Pro Gly Leu Val Arg Pro Ser Gln Thr Leu
1               5                   10                  15

Ser Leu Thr Cys Thr Val Ser Gly Phe Thr Ile Ser Ser Gly Tyr Ser
                20                  25                  30

Trp His Trp Val Arg Gln Pro Pro Gly Arg Gly Leu Glu Trp Ile Gly
            35                  40                  45

Tyr Ile Gln Tyr Ser Gly Ile Thr Asn Tyr Asn Pro Ser Leu Lys Ser
        50                  55                  60

Arg Val Thr Met Leu Val Asp Thr Ser Lys Asn Gln Phe Ser Leu Arg
65                  70                  75                  80

Leu Ser Ser Val Thr Ala Ala Asp Thr Ala Val Tyr Tyr Cys Ala Arg
                85                  90                  95

Glu Asp Tyr Asp Tyr His Trp Tyr Phe Asp Val Trp Gly Gln Gly Ser
            100                 105                 110

Leu Val Thr Val Ser Ser
            115

(2) INFORMATION FOR SEQ ID NO:7:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GGTGTCCACT CCGACATCCA GATGACCCAG AGCCCAAGCA GCCTGAGCGC CAGCGTGGGT      60

GACAGAGTGA CCATCACCTG TAGTACCAGC TCGAGTGTAA GTTACATGCA CTGGTACCAG     120

CAGAAGCCAG GTAAGGCTCC AAAGCTGCTG ATCTACAGCA CATCCAACCT GGCTTCTGGT     180

GTGCCAAGCA GATTCAGCGG TAGCGGTAGC GGTACCGACT TCACCTTCAC CATCAGCAGC     240

CTCCAGCCAG AGGACATCGC CACCTACTAC TGCCATCAGT GGAGTAGTTA TCCCACGTTC     300

GGCCAAGGGA CCAAGGTGGA AATCAAACGT                                     330

(2) INFORMATION FOR SEQ ID NO:8:

(i) SEQUENCE CHARACTERISTICS:
        (A) LENGTH: 110 amino acids
        (B) TYPE: amino acid
        (D) TOPOLOGY: linear (ii) MOLECULE TYPE: peptide (xi) SEQUENCE DESCRIPTION: SEQ ID NO:8:

Gly Val His Ser Asp Ile Gln Met Thr Gln Ser Pro Ser Ser Leu Ser
1               5                   10                  15

Ala Ser Val Gly Asp Arg Val Thr Ile Thr Cys Ser Thr Ser Ser Ser
                20                  25                  30

Val Ser Tyr Met His Trp Tyr Gln Gln Lys Pro Gly Lys Ala Pro Lys
            35                  40                  45

Leu Leu Ile Tyr Ser Thr Ser Asn Leu Ala Ser Gly Val Pro Ser Arg
        50                  55                  60

Phe Ser Gly Ser Gly Ser Gly Thr Asp Phe Thr Phe Thr Ile Ser Ser

-continued

```
              65                  70                  75                  80
Leu Gln Pro Glu Asp Ile Ala Thr Tyr Tyr Cys His Gln Trp Ser Ser
                    85                  90                  95
Tyr Pro Thr Phe Gly Gln Gly Thr Lys Val Glu Ile Lys Arg
               100                 105                 110
```